(12) United States Patent
Draper et al.

(10) Patent No.: US 6,262,270 B1
(45) Date of Patent: Jul. 17, 2001

(54) ENANTIOSELECTIVE SYNTHESIS

(75) Inventors: Richard W. Draper, North Caldwell; Radha V. Iyer, Edison, both of NJ (US); Yuelie Lu, Thousand Oaks, CA (US); Eugene J. Vater, Lyndhurst, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/371,172

(22) Filed: Aug. 11, 1999

Related U.S. Application Data

(60) Provisional application No. 60/096,552, filed on Aug. 14, 1998.

(51) Int. Cl.[7] ...................... C07D 405/10; C07D 405/12
(52) U.S. Cl. ........................................... 546/196; 514/320
(58) Field of Search .............................. 514/320; 546/196

(56) References Cited

U.S. PATENT DOCUMENTS

| | | | |
|---|---|---|---|
| 5,395,842 | 3/1995 | Labrie et al. | 514/320 |
| 5,407,947 | 4/1995 | Bryant et al. | 514/320 |
| 5,446,061 | 8/1995 | Bryant et al. | 514/456 |

FOREIGN PATENT DOCUMENTS

| | | |
|---|---|---|
| WO 93/10741 | 6/1993 | (WO) . |
| WO 96/26201 | 8/1996 | (WO) . |

OTHER PUBLICATIONS

Sharma, Structure–Activity Relationship of antiestrogens. Phenolic Analogues of 2,3–Diaryl–2H–1–benzopyrans, J. Med. Chem., 1990, 33, pp. 3222–3229.

Sharma, Structure–Activity Relationship of Antiestrogens. Effect of the Side Chain and Its Position on the Activity of 2,3–Diary–2H–1 benzopyrans, J. Med. Chem., 1990, 33, pp. 3216–3222.

Button, The Reversible Cyclisation of a Chalcone, 1(2–Hydroxy–4, 6–dimethoxphenyl)–3(4–ethoxphenyl)prop–2–en–1–one: a Kinetic and Mechanistic Study, J. Chem. Soc. Perkin Trans., 2, 1992, pp. 1571–1580.

Imamoto, Cerium Chloride–Promoted Necleophilic Addition of Grignard Reagents to Ketones an Efficient Method for the Synthesis of Tertiary Alcohols, Tetrahedron Letters, vol. 26, No. 39, 1985, pp. 4763–4766.

Kabbe, Synthesis and Reactions of 4–Chromanones, Angew, Chem. Int. Ed. Engl. 21, 1982, pp. 247–256.

Wahala, Expedient Synthesis of Polyhydroxyisoflavones, J. Chem. Soc. Perkins Trans., 1991, pp. 3005–3008.

Miles, Kinetics and Mechanism of the Cyclisation of 2',6'–Dihydroxychalcone and Derivatives, J. Chem. Soc. Perkin. Trans., II, 1989, pp. 1623–1632.

Cisak, Practical and Theoretical Aspects of Flavanone–Chalcone Isomerisations, J. Chem. Soc. Perkin Trans., 2, 1992, pp. 1603–1607.

Harwood, An Improved Procedure for Cyclisation of Chalcones to Flavonones Using Celite Supported Potassium Fluoride in Methanol: Total Synthesis of Bavachinin,Synthetic Communications, 20(5), 1990, pp. 649–657.

Hughes, Some Hypocholesterenic 2,3–Diphenylacrylonitriles, J. Med. Chem. 7(4), 511–518 (1964).

Brennan, Stereoelectronic effects in ring closure reactions: the 2'–hydroxychalcone—flavanone equilibrium, and related systems, Can. J. Chem., vol. 68, 1990, pp. 1780–1785.

Gauthier et al. "S–(+)–4–7–(2, 2–dimethyloxproposy–4–methyl–2–. . . " J. Med. Chem. v.40, 2117–2122, 1997.*

\* cited by examiner

*Primary Examiner*—Ceila Chang
(74) *Attorney, Agent, or Firm*—Thomas D. Hoffman

(57) ABSTRACT

A short practical commercial process for the efficient enantioselective synthesis of the non-steroidal antiestrogen of formula I or XIV

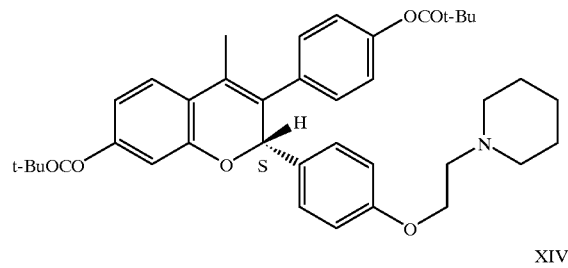

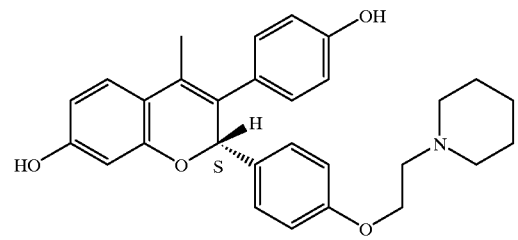

or a pharmaceutically acceptable salt thereof.

22 Claims, No Drawings

ENANTIOSELECTIVE SYNTHESIS

This application claims priority of Provisional Application No. 60/096,552 filed Aug. 14, 1998.

BACKGROUND OF THE INVENTION

The present invention relates to a short efficient enantioselective synthesis of the orally active a antiestrogen of the formula I or XIV

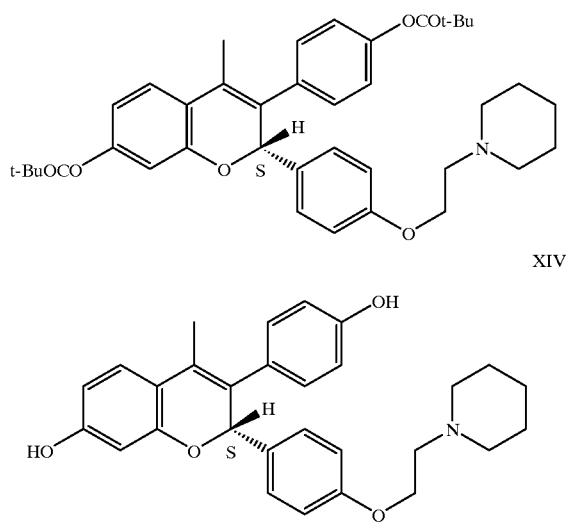

or a pharmaceutically acceptable salt thereof.

The synthesis and the antiestrogenic activity of the compound of formula 1, i.e., (S)-7-hydroxy-3-(4'-hydroxyphenyl)-4-methyl-2-(4"-[2"'-(1-piperidino)-ethoxy]phenyl)-2H-benzopyran 4',7-bistrimethylacetate, is disclosed in *J. Med Chem.*, 1997, 40, 2117–2122. See also U.S. Pat. Nos. 5,395,842, and 5,407,947 and *J. Med. Chem.*, 1990, 33, 3216–3222. Each of the synthetic schemes disclosed is a laboratory scale procedure involving costly steps not suitable for a practical commercial scale process.

There is a need for a short, efficient, enantioselective synthesis suitable for the large scale manufacture of the compounds of formulas I and XIV.

SUMMARY OF THE INVENTION

The present invention provides a process which comprises reacting the compound of formula IV with the compound represented by formula VII

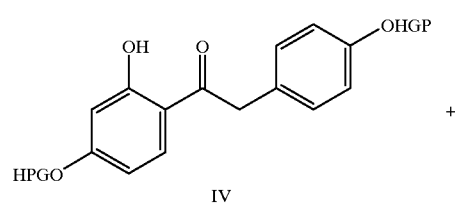

+

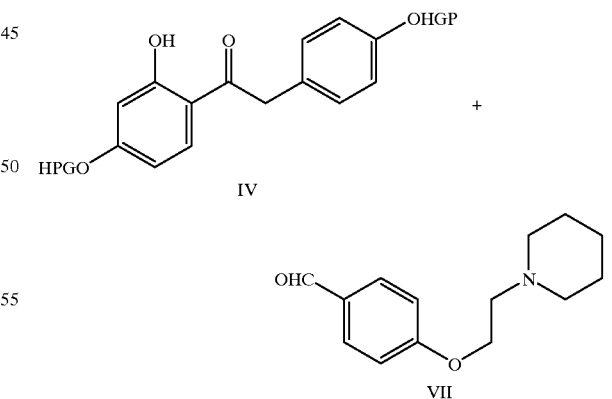

in the presence of piperidine, a hindered organic amine base and a ($C_3$–$C_6$) alkanol at temperature and for a time sufficient to produce the compound of formula IX essentially free of the cis-isomer of the compound of formula IX, and of the E and Z-chalcones of formula VIII wherein HPG is an acid-labile phenolic hydroxyl protecting group:

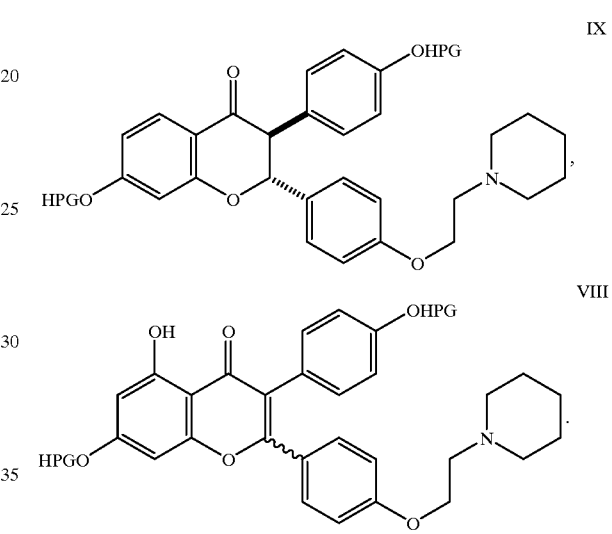

The present invention also provides a process which comprises the steps of:

(a). reacting the compound of formula IV with the compound represented by formula VII:

in the presence of piperidine, a hindered organic amine base and a ($C_3$–$C_6$) alkanol at temperature and for a time sufficient to produce the compound of formula IX essentially free of the cis-isomer of the compound of formula IX, and substantially free of the E and Z-chalcones of formula VIII wherein HPG is an acid labile phenolic hydroxyl protecting group;

IX

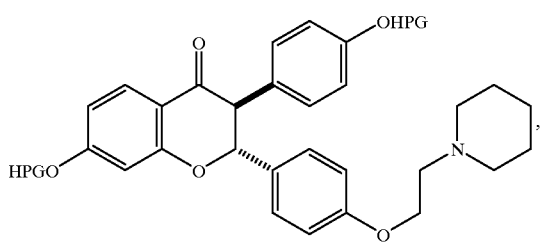

VIII

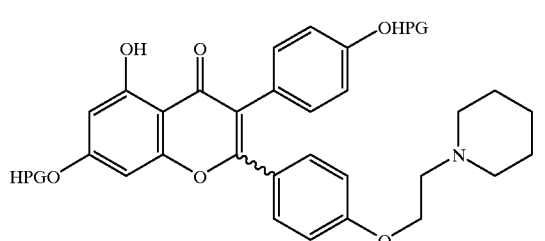

(b). reacting the compound of formula IX with a stoichiometric excess of methyl lithium in an aprotic solvent for a time and temperature sufficient to produce the compound of formula X;

X

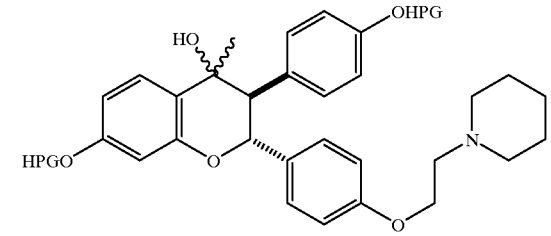

(c). contacting the compound of formula X with a stoichiometric excess of (S)-(+)-camphorsulfonic acid in a solvent comprising a $C_1$–$C_6$ alkanol for a time and at a temperature sufficient to produce the racemic R,S/S,S-acid addition salt of the formula XI;

XI

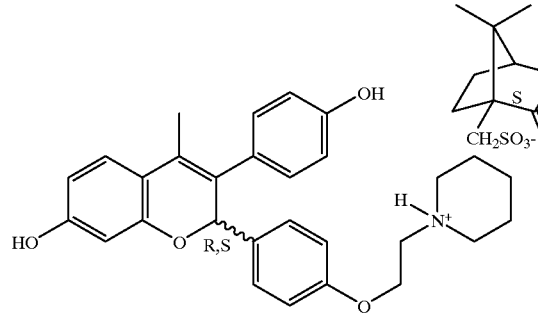

(d). contacting the racemic acid addition salt of the formula XI with a catalytic amount of (S)-(+)-camphorsulfonic and in a solvent comprising ethanol for a time and at a temperature sufficient to produce the single S,S-diastereometric acid addition salt of the formula XII;

XII

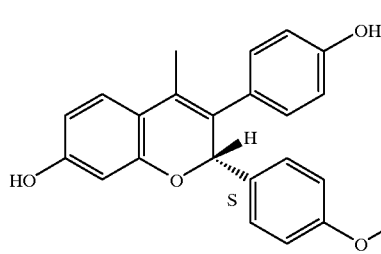

substantially free of the opposite R,S-diastereomeric salt of the formula XIII,

XIII

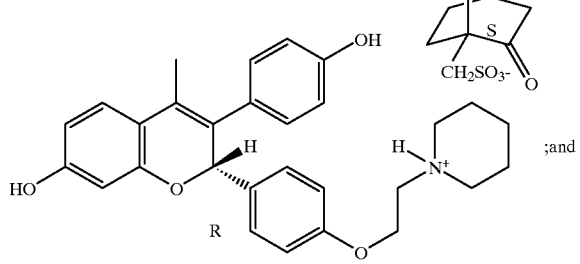

;and (e)(i). contacting the the S,S-diastereometric acid addition salt of compound XII with a stoichiometric excess of pivaloyl chloride in the presence of tertiary organic base at a temperature and time sufficient to produce the compound of formula I:

I

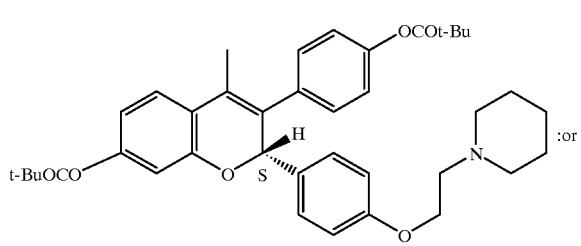

:or (e)(ii) contacting the the S,S-diastereometric acid addition salt of compound XII with sufficient amount of a tertiary organic base at a temperature and time sufficient to produce a compound of formula XIV:

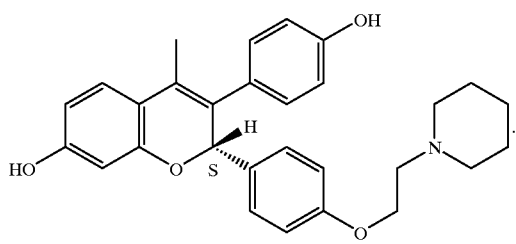

DETAILED DESCRIPTION OF THE INVENTION

The process of the present invention provides a short, practical commercial process for the efficient enantioselective synthesis of the potent orally active nonsteroidal, antiestrogen compounds of formulas I and XIV, substantially chemically and enantiomerically pure. By the term "enantioselective synthesis" as used herein in reference to the compounds of formulas I and XIV is meant that the process of this invention produces the S-enantiometer of formulas I and XIV in preference to the enantiomer of the opposite R-configuration. The process, summarized in Schemes I and IA, comprises a selection of reagents and reaction conditions which avoid the use of separation techniques such as fractional crystallization and chromatography while providing chemically and enantiometrically pure compounds. Steps B and C of the process in Scheme I involves reactions and reactions conditions to shift the chalcone (compound VIII)/chromanone-(compound IX) equilibrium to produce essentially only the pivotal 2,3-trans-diaryl-2,3-dihydro-4H-1-benzopyran-4-one of formula IX a precursor of the compound of formula 1. The conversion of this racemic precursor to a single S,S-diastereomer of formula XII is effected by a kinetic (dynamic) resolution in Step F. Specifically, the present invention provides conditions and reagents in Steps B and C which allow production of a single trans compound of formula IX substantially chemically pure and essentially free of the cis-isomer of the compound of formula IX and free of the E and Z chalcones of formula VIII. By the term "chemically pure" as used herein means greater than 95% preferably greater than 99% free of other chemicals, e.g. the E and Z chalcones of formula VIII. By the phrase "essentially free of the cis-isomer of compound of the formula IX" as used herein means that the compound of formula IX contains less than about 2% preferably less than about 1% of the cis-isomer of the compound of the formula IX.

By the term "($C_3$–$C_6$) alkanol" is meant a straight or branched chain ($C_3$–$C_6$) alkanol including isopropanol isobutanol, isopentanol and isohexanol, and the secondary alcohols, 2-butanol, 2-pentanol, 3-pentanol, and 2-hexanol. Use of 2-butanol, isobutanol or isopropanol are preferred. Use of 2-butanol is more preferred.

By the term "acid labile phenolic hydroxyl protecting group" (HPG) as used herein is meant means protecting groups which are removed under acidic conditions, e.g., conditions of step E of the present invention. Typically suitable acid labile phenolic hydroxyl protecting groups include phenolic protecting groups commonly employed in organic chemistry including, but not limited to, tetrahydropuranyl, methoxymethyl, methoxyethoxymethyl and cyclopropylmethyl. The introduction of phenolic hydroxyl protecting groups is disclosed in "Protecting Groups in Organic Synthesis, T. W. Greene, pp. 87–113. J. Wiley & Sons, NY, 1984. Use of tetrahydropyranyl as a phenolic hydroxyl protecting group is preferred. (See Example 1.)

By the term "a hindered organic amine base" as used herein means non-nucleophilic organic amines. Typically suitable hindered organic amine bases include 1,5-diazabicyclo[4.3.0]non-5-ene ("DBN"), 1,4-diazabicyclo[2.2.2.]octane ("Dabco™"), 1,8-diazabicyclo[5.4.0]undec-7-ene ("DBU") and 1,1,3',3'-tetramethylguanidine ("TMG"). DBN, Dabco, DBU and TMG are available from Aldrich, Milwaukee Wis. 53233. Use of DBU and DBN are preferred. Use of DBU is more preferred.

By the term "tertiary amine base" as used herein means tri ($C_1$–$C_6$) alkyl amines such as triethylamine, N-methylpiperidine and N-methyl morpholine. The preferred tertiary amine base is triethylamine.

Scheme I

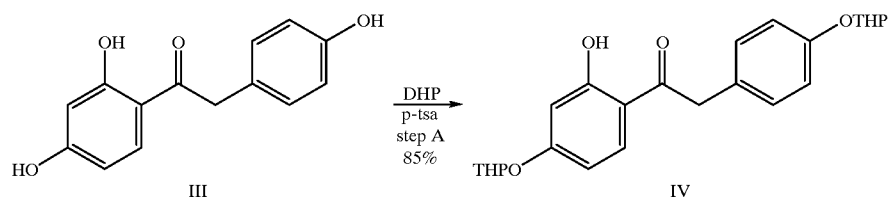

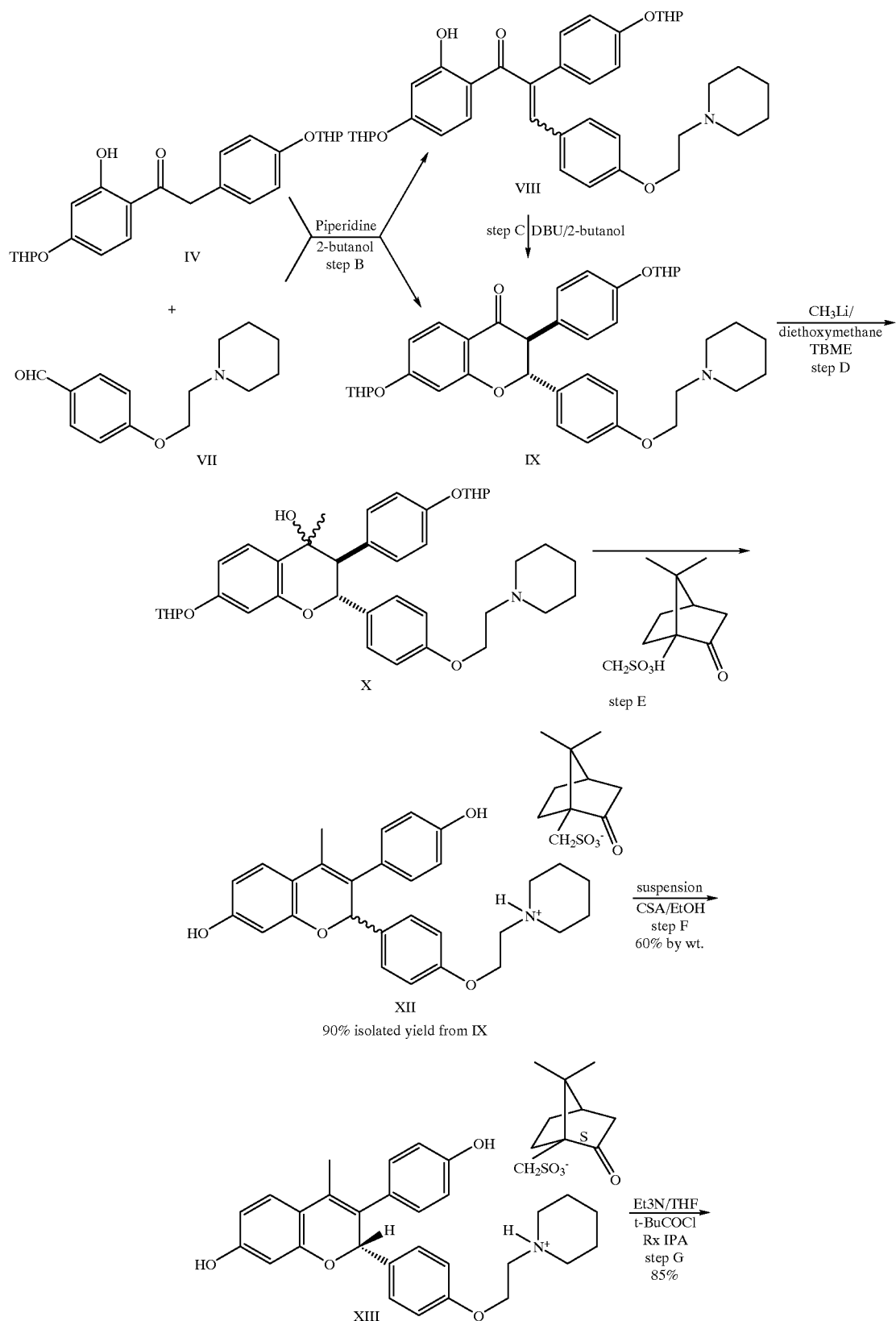

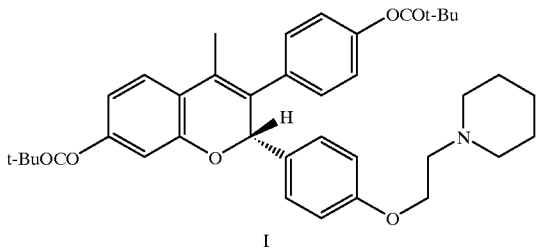

I

Scheme IA

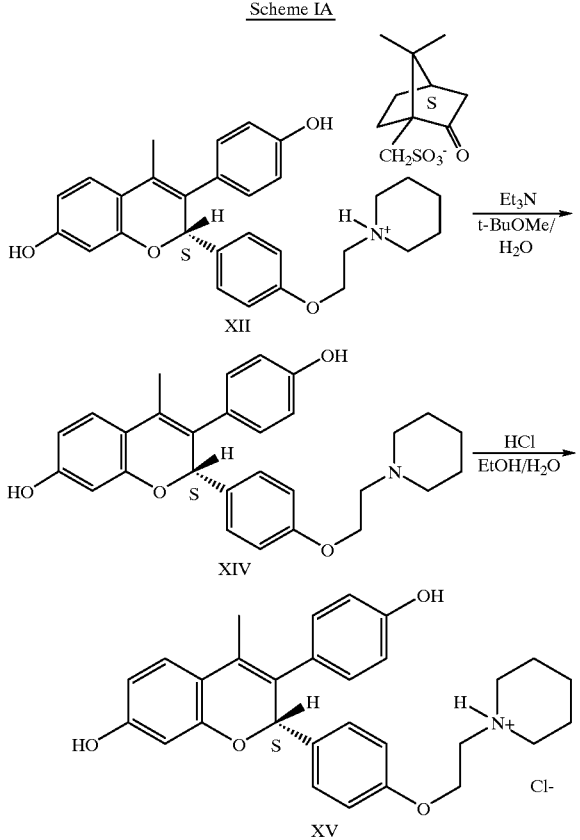

Details of the steps in the Schemes I and IA are provided herein below.

Step A: The compound of formula IV may be prepared by reaction of the compound of formula III with dihydropyran ("DHP") in the presence of p-toluenesulfonic acid ("p-tsa") in ethyl acetate. The compound of formula III may be prepared as described in *J. Med. Chem.*, 1997, 40, 2117–2122 at page 2117.

Steps B and C: Step B, formation of the carbon-carbon double bond in compound of the formula VIII, involves a Knoevenagel condensation reaction of the ketone compound of formula IV with the aldehyde of formula VII in the presence of a solvent and a catalytic amount of piperidine. The preferred solvent is 2-butanol but other ($C_3$–$C_6$) alkanols such as isopropanol or isobutanol may also be used. The condensation reaction is normally carried out by heating the reacton mixture of compounds IV and VII and piperidine in a ($C_3$–$C_6$)alkanol to reflux temperature under an inert atmosphere such as nitrogen or argon. The Knoevenagel condensation is an equilibrium reaction and must be driven to completion by removal of water from the reaction mixture. Removal of water is achieved by distilling out an azeotropic mixture of alcohol and water. Water formed in the reaction may also be removed by use of a drying agent such as molecular sieves or anhydrous sodium sulfate. The drying agent, if used, may be added to the reaction or be contained in an external vessel such as a column through which the azeotropic distillate of alcohol and water passes before being returned to the reaction mixture. Alternatively, other solvents such as the aromatic hydrocarbons, e.g., toluene or xylene, in which water is immiscible, may also be used as a solvent in the Knoevenagel reaction. When aromatic hydrocarbons are used as solvents, water may be removed during reflux by means of a Dean-Stark trap. If these aromatic hydrocarbon solvents are used, however, they must be replaced with an ($C_3$–$C_6$) alkanol as described above before carrying out the isomerization of step C. This isomerization of the compounds of formula VIII to the compound of formula IX is also a base-catalysed equilibrium process wherein the equilibrium position is dependent upon the temperature, solvent and base involved in the process. At the completion of the Knoevenagel reaction, the ratio of VII to IX is about 1.6:1 to 2:1 depending upon the solvent used. We have discovered that with the use of a strong hindered organic amine base such as DBU or DBN in a ($C_3$–$C_6$) alcohol, preferably 2-butanol or 2-propanol, this equilibrium ratio may be raised to about 6:1 which is still not sufficiently high for a manufacturing process which should avoid chromatagraphy or other inefficient methods of purification to be commercial feasible. We have further discovered that if the concentration of VII and IX in the ($C_3$–$C_6$) alkanol is adjusted so that trans-chromanone of formula IX crystallises out during the isomerization, the equilibrium can be driven completely towards compound IX. Ultimately, at the end of the isomerization step, the ratio of IX to VII in the reaction mixture is about 98:2 and in the product which crystallizes out said ratio of IX to VII is greater than 99:1. The use of a hindered organic amine base such as DBU or DBN as opposed to the prior art bases, e.g., sodium or potassium acetate advantageously also reduces by-products arising from deprotection of the phenolic hydroxy groups. After the Knoevenagel reaction is complete, the reaction mixture is cooled and the concentration of products is adjusted by adding or removing the alcohol as necessary. If a solvent other than a ($C_3$–$C_6$) alcohol is used, then this non-alcoholic solvent is removed by distillation and replaced with a suitable ($C_3$–$C_6$) alcohol. In Step C, the so-formed mixture of cis- and trans-chromanones of formula IX and E and Z chalcones of formula VIII is stirred at room temperature for a time sufficient—preferably at least 24 hours but as much as 48 hours—to complete the isomerization of the mixture to the pure trans-compound of formula IX. Seeds of IX may be added, if necessary, to ensure crystallization of IX occurs. IX is filtered and washed with isopropanol or 2-butanol. The DBU or DBN is normally and preferably added after the Knoevenagel condensation reaction is complete (i.e., after the reaction mixture is cooled to room temperature) and before the start of Step C. DBU or DBN also may optionally be added with the piperdine at the start of Step B. The catalytic amounts of piperidine and the strong hindered organic amine base such as DBU used are normally about one-third of the stoichiometric amount of IV used in the reaction (See Example 1).

The prior art process described in *J. Med. Chem,* 1997, 40 2117–2122 at 2118 produces a mixture of compounds IX and VIII in a ratio of 3:2 (60% to 40%). In accordance with the process of this invention, VIII is converted completely into the trans-compound of formula IX which is substantially chemically pure and is essentially completely free (i.e. containing less than about 2 or even 1%) of the cis-isomer of the formula IX and the E&Z isomers of the formula VIII.

Step D: The preferred organometallic reagent for the methylation Step D is methyl lithium but methyl magnesium halide, preferably methyl magnesium chloride or bromide in the presence of ceric (III) chloride may also be used. Use of methyl lithium ("MeLi") is preferred.

We have discovered that during Step D, the methylation of the compound of formula IX, compound IX isomerizes back to the chalcones of formula VIII. In the presence of methylating agents, chalcones of formula VII can give rise to compounds of formula Q, i.e., products of 1, 4 addition to the enone.

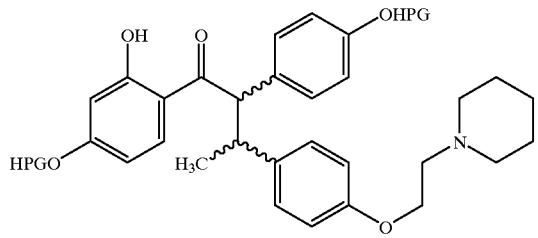

Under the prior art conditions which include use of methyl magnesium halides in THF or ether (see U.S. Pat. Nos. 5,395,842, or 5,407,947 and *J. Med. Chem.,* 1990, a p 3216–3222), VIII and Q are obtained in a ratio of about 7:1 and are normally separated by chromatography. Mixtures of VIII and Q are also obtained with MeLi in THF alone (See *J. Med. Chem.,* 1997, 40 p. 2117–2122) and chromatography is normally required to separate these mixtures into pure compounds. We have found that under certain conditions chromanones of formula IX can be methylated such that less than about 3% of compounds of formula Q are formed the (ratio of IX to Q is greater than about 27:1). No chromatography is required as the small amount of Q is conveniently removed in the next step i.e. Step E during crystallization of XI. To achieve this low level of Q, methylation is carried out in a non-polar acyclic ether solvent using methyllithium as the methylating reagent and a non-polar ether solvent such as diethyl ether, t-butylmethyl ether, dimethoxyethane or diethoxymethane under anhydrous conditions. The preferred acyclic ether solvent is t-butylmethyl ether. Use of a cyclic ether, e.g. THF, as the sole solvent normally leads to larger quantity of compounds of formula Q. Other non-polar solvents such as toluene or cumene may be used but are not as convenient since they have relatively high boiling points and are difficult to remove. Mixtures of the above-listed anhydrous acyclic ethers with anhydrous aromatic hydrocarbons such as cumene or toluene; preferably a mixture of cumene and THF may also be used. Preferred aprotic solvents are neat anhydrous ethers, especially diethoxymethane ("DEM") and t-butyl methyl ether ("TMBE"). At least about 2.8 equivalents, preferably about 3 equivalents of MeLi are required in Step D; lesser amounts of MeLi lead to larger amounts of Q. The preferred methylation reagent is methyllithium as an 8% solution in DEM. Other commercialy available sources of methyllithium such as methyllithium 1.4M in diethyl ether or methyllithium 1.0M in cumene/THF (9:1,v/v) may be utilized but are less preferred as they are more dilute, i.e., have a lower concentration of the methylation reagent, and they also give more of Q. The methylation is preferably run under a dry, oxygen-free inert atmosphere such as dry nitrogen or argon. The methylation reaction temperature is normally in the range of about –20° C. to about 50° C., preferably about –200° C. to 20° C., and most preferably in the range of about 0° C. to about 50° C. under anhydrous, inert atmosphere conditions. The prior art methylation was run at a temperature of –78° C.

In accordance with a preferred aspect of the process of this invention, methyl lithium as an 8% solution in diethoxymethane ("DEM") is used with tert-butylmethyl ether ("TBME") as a reaction solvent to produce alkylation by methyl lithium almost solely at the carbonyl carbon with less than 1–2% of Q formed by 1,4 Michael alkylation of VIII. The reaction is preferably run under an inert atmosphere of nitrogen or argon at a temperature in the range of about –0 to about 5° C. The reaction is quenched with an aqueous acid solution—preferably aqueous ammonium chloride and the organic layer containing compound X is washed with brine and forwarded to the next step without further purification or chromatography as is taught in *J. Med. Chem* 1997, 40, 2117–2122 at 2117. Also *J. Med. Chem.* 1990 33 3216.

Step E: The prior art dehydration and deprotection procedure (removal of preferred THP acid-labile phenolic hydroxyl protecting groups) of the compound of formula X uses 90% acetic acid at 90° C. to produce the free base of the diphenol of formula Z. This prior art dehydration-deprotection procedure suffers from the difficulty of removing acetic acid from the product of formula Z and production of amorphous material of variable light pink to red color due to the formation impurities. The free base reaction product of formula Z contains large amounts of solvent and is also unstable. The prior art high reaction temperature is detrimental and causes increased decomposition of the deprotected diphenol Z. The prior art process also requires chromatography to purify the free base compound of formula Z.

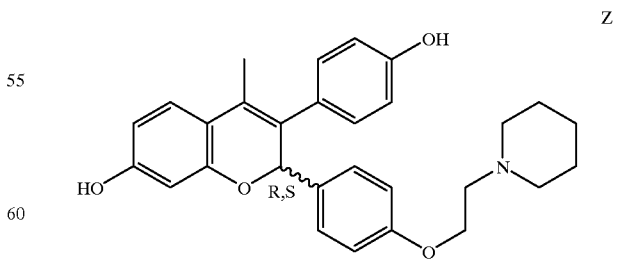

We have discovered a novel process by which the dehydration and deprotection is accomplished in Step E. The process is rapid and conducted at a room temperature to reduce the formation of impurities. Furthermore, the diphenol, free base of formula Z once formed is converted immediately without isolation to the racemic (S)-camphorsulfonic acid addition salt of formula XI which is more stable than the diphenolic, free base Z. A further advantage of Step E is that the composition of formula XI is produced as a solid crystalline material and may be isolated in high yield and readily purified by crystallization directly from the reaction solvent, without the need of any costly chromatography. The racemic (S)-camphorsulfonic acid addition salt composition of formula XI is a new composition of matter, not previously isolated or described. The process of Step E is carried out as follows. The TBME solution of the compound of formula X from the previous Step D is concentrated and the so-formed residue dissolved in an inert solvent such as a lower alcohol, including for example methanol, ethanol or isopropanol or a ketone or mixture of alcohols, preferably ethyl alcohol, most preferred mixture of ethyl alcohol, methyl alcohol and isopropanol (18:1:1,v/v/v). The concentration of X is preferably in the range of about 1000 g/L to about 200 g/L most preferred about 340 g/L. At least about 1.0 to about 1.5 equivalents, preferably about 1.1 equivalents of (S)-camphorsulfonic acid ["(S)-CSA"] is added and the solution stirred at room temperature for 24–48 hours, preferably about 24 hours while the racemic (S)-CSA acid addition salt composition of formula XI crystallizes. An additional solvent such as isopropanol may be optionally added to maintain fluidity during crystallization. The racemic R,S/S,S composition of formula XI is filtered off, washed with an alcohol solvent, other than methanol, such as isopropanol and dried. The process is preferably run under an inert atmosphere such a argon or nitrogen. Isolation of the composition of formula XI as a crystalline solid has the further advantage of allowing its use in a novel dynamic resolution process in Step F described below.

In a preferred embodiment of Step E, the compound of formula X is dehydrated, deprotected and the so-informed diphenol converted into a mixture of diastereomeric acid addition salts of formula XI by contacting X with a stoichiometric excess at least about 1.0 to 1.5 equivalents, preferably about 1.1 equivalents of (S)-CSA at room temperature in a solvent comprising ethanol, preferably ethanol denatured with 5% (v/v) methanol and 5% (v/v) of isopropanol. The so-formed reaction mixture is stirred for about 15 minutes and the mixture of diasterometric acid addition salts of formula XI starts to crystallize. When the crystallization is well under way and the slurry becomes quite thick, five volumes of isopropanol are added and the slurry is stirred for at least 24 hours at about 20° C. The crystalline mixture of the diastereomeric acid addition salts of formula XI is isolated by filtration and dried in a draft oven below 50° C. to produce a 90% yield (from compound IX) of the mixture of S,S-R,S-diastereomeric-(S)-CSA acid addition salts of formula XI which are 97.8% chemically pure.

Step F: In the prior art process, separation of the racemic free base compound of formula Z into its constituent R&S enantiomers was carried out either by costly and time-consuming chromatography using a chiral stationary phase or by a traditional resolution via fractional crystallization of a mixture of diastereomeric (S)-camphorsulfonic acid salts prepared in situ by adding (S)-camphorsulfonic acid to the compound of formula Z in a mixture of $CH_2Cl/DMF$. This prior art process also uses the chlorinated hydrocarbon, $CH_2Cl_2$, which is expensive and hazardous. The yield in the prior art resolution is low and the undesired R,S diastereomer is wasted or must be recycled via a lengthy process which involves a high temperature lithium hydroxide base-catalysed racemization to produce the free base diphenol compound of formula Z which must be then converted again in situ to the racemic (S)-camphorsulfonic acid salt of formula XI and re-resolved as before.

We have invented a novel dynamic resolution process (Step F) for the compound of formula XI which not only circumvents the disadvantages of the prior art process but also gives superior optical and chemical yields. The present invention provides in Step F a superior novel dynamic resolution process that not only circumvents the disadvantages of the prior art processes but that also provides the S,S-diastereomer of the salt compound of formula XII in higher yield and optical purity. A special feature of this dynamic resolution process is the simultaneous resolution of the diastereomeric mixture of (S)-camphorsulfonic acid addition salts of formula XI and the racemization of the undesired R,S-diastereomer of the compound of formula XII such that up to 130% of the amount of the S,S-diastereomer of XII in the original R,S-S,S-diastereomeric acid addition salt starting mixture of formula XI is obtained. This dynamic resolution process avoids the disadvantages of the prior art methods described above, including the need for chromatography which is impractical on a very large scale and the need for a separate base-catalysed racemization step together with the requirement of reforming the diastereomeric (S)-camphorsulfonic acid salt of formula XI in order to recover and recycle the undesired, opposite R,S-diastereomer of compound of formula XIII:

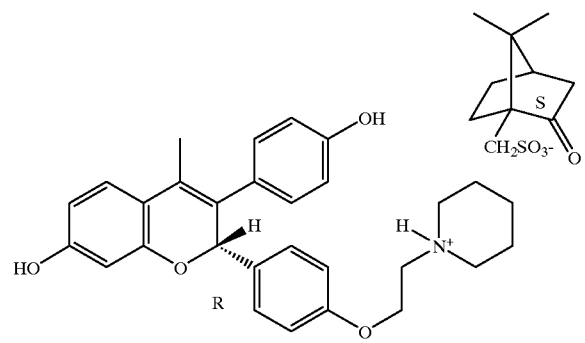

XIII

Our improved dynamic resolution process also avoids the use of $CH_2Cl_2/DMF$ solvent mixture of the prior art resolution process and at the same time increases the optical purity of the compound of formula XII to 99% diastereomeric excess ("de")—prior art process produced only 92% de—and the weight yield to greater than 60% (vs 41% for the prior art process).

Step F of the process of the present invention is characterized by heating a suspension of the diastereomeric mixture of the (S)-camphorsulfonic salts of formula XII in about 6 volumes of (range 4 to 8 volumes) ethanol preferably anhydrous 2B ethanol(95% ethanol-5%water) containing (S)-camphorsulfonic acid in a catalytic amount of from about 0.15 mole equivalents to about 1.2 mole equivalents, preferably about 05 to about 0.7 mole equivalents, most preferably 0.6 mole equivalents (about 20 weight %) of (S)-camphorsulfonic acid at a temperature between 50° and the boiling point of ethanol, preferably a temperature in the range of about 70–80°, more preferably about 70° and 75° C. for a time until the S,S:R,S ratio of diastereomeric (S)-camphorsulfonic acid salts of formula XI in the total reaction mixture is about 7:1 (usually less than 24 hours). The reaction mixture is preferably agitated under an inert atmosphere such as nitrogen or argon during the heating and cooling process. The reaction mixture is cooled to room temperature for about 4 to 24 hours, preferably for about 4 to 6 hours, then the optically pure diphenol (S)-camphorsulfonic salt of formula XII is isolated by filtration and washed with an alcohol such as ethanol or isopropanol and dried.

We believe that the undesired R,S-diastereomer of the acid addition salt of formula XIII is solubilized during this acid catalysed process and is racemized at the 2-position of the 2H-benzopyran ring system to generate a mixture of S,S and R,S (S)-camphorsulfonic acid addition salts of formula XI. The less soluble S,S diastereomer acid addition salt crystalizes out allowing more of the R,S diastereomer to go into solution. In this manner the R,S/S,S salt equilibrium is forced over mainly to the S,S form, namely the compound of formula XII.

Step G: in the prior art process, the (S)-camphorsulfonic acid salt compound of formula XII was first converted into the (S)-enantiomer free base compound of formula Z by treatment with aqueous $K_2CO_3$, isolated by extraction into a solvent, the so-formed solution was dried and concentrated. In a second step, the (S)-enantiomer free base compound of formula Z was converted by treatment with pivaloyl chloride and triethylamine in methylene chloride into the compound of formula I. On a large scale, this method is wasteful of extracting solvent, is time-consuming and can lead to decomposition of the unstable free base of formula Z during the lengthy processing. Furthermore we have observed that the compound of formula I reacts with $CH_2Cl_2$ to generate an undesirable impurity chloromethyl quarternary salt of formula $Z_2$.

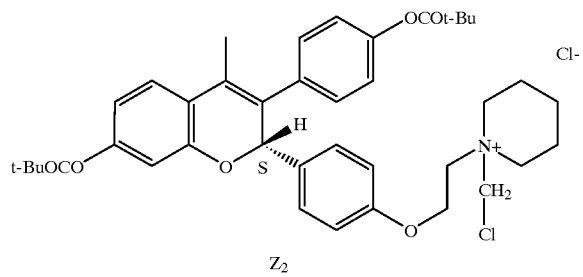

$Z_2$

Step H: In Step H of Scheme 1A, compound XV, the hydrogen chloride acid addition salt of compound XIV, may be prepared directly from compound XII by free basing the (S)-camphorsulfonate salt (XII) to afford compound XIV which is, without isolation, converted to compound XV. Compound XV may be optionally purified by recrystallization. Freebasing is carried out by suspending salt XII in a mixture of water and an immiscible organic-solvent, in which the free base (Compound XIV) is soluble and adding between one and two equivalents (preferably about 1.4 equivalents) of a base such as an akali metal carbonate or bicarbonate or preferably a tertiary organic base, such as a trialkylamine or pyridine, preferably triethylamine. The immiscible organic solvent may be an ether, ketone, ester, halogenated hydrocarbon, preferably an ether or ester, most preferably t-butylmethylether (t-BuOMe) The so-formed mixture is agitated, preferably at ambient temperature, until complete solution has occurred. The lower aqueous layer is separated and extracted with the organic solvent. All the organic solvent and extracts containing compound XIV are combined and washed with brine and filitered through silica gel. The filtrate is concentrated and the solvent replaced with a water miscible alcohol solvent, preferably ethanol.

The alcohol solution of compound XIV is cooled, preferably to about 5° C. and between one and two equivalents (preferably about 1.1 equivalents) of 2N hydrochloric acid are added slowly with agitation about 3. Agitation is continued for 30 minutes and then water is added. Agitation is continued for about a further 1 to 6 hours, preferably about 2 hours, during which time the temperature is maintained between about 0 and 25° C. preferably about 5 to 10° C. The crystals of compound XV are filtered off, washed with water and dried at room temperature under vacuum with a slow nitrogen flow. Compound XV may be optionally recrystallized from a water miscible alcohol solvent and water, preferably ethanol and water, most preferrably ethanol/water (1:4,v/v).

The process of the present invention has been designed to avoid the prior art disadvantages described above in that the (S)-enantiomer of the free base of formula Z is not isolated in the process of the present invention but rather is generated in situ from the precursor of the formula XII and is immediately converted into the (S)-enantiomer of the bispivaloate of formula I. The process of the present invention has the further advantages of producing the compound of formula I in higher optical and chemical purity and also in higher yield than the prior art processes. Since the process of the present invention also avoids the use of methylene chloride, the compound of formula I is additionally uncontaminated with the impurity of formula $Z_2$.

The process of Step G is normally carried out by suspending the compound of formula XII in about 2–8 volumes of THF, preferably anhydrous THF. To this suspension is added a stoichiometric excess of triethylamine. About 3 to about 6 equivalents, preferably about 3 to about 4.5 equivalents, and most preferably about 4.1 equivalents of triethylamine are used. The so-formed solution is cooled to a temperature in the range of about –30° C. and about 0° C., preferably about –20° C. to –15° C. A solution of about 2 equivalents to 4 equivalents, preferably about 2.9 equivalents of pivaloyl chloride (trimethylacetyl chloride) in about 1 volume of THF, preferably anhydrous THF (relative to quantities of XII), is added to the cooled solution. The mixture is preferably agitated under an inert atmosphere such as nitrogen or argon during the reaction. The reaction mixture is allowed to proceed until it is substantially complete, preferably keeping the temperature below about 15° C. The compound of formula I is then conveniently isolated by diluting the reaction mixture with an inert, water-immiscible, low boiling solvent (other than a halogenated hydrocarbon), preferably t-butylmethyl ether, washing the reaction mixture with an aqueous solution of a mild base, such as sodium bicarbonate or potassium carbonate, preferably sodium bicarbonate to destroy the excess pivaloyl chloride. The solvent is normally then removed by evaporation to obtain the compound of formula I.

The process of the present invention also encompasses a final purification step for the compound of formula I. The purification step normally involves crystallization of the compound of formula I from a lower alcohol other than methanol such as isopropanol or 2-butanol, preferably 18 volumes of isopropanol. The crystallization optionally includes contacting the alcohol solution of the compound of formula I with activated charcoal, filtering the charcoal, concentrating and cooling the purified solution to obtain crystals of the compound formula I which may be isolated by filtration. In this manner, the compound of formula I is obtained substantially chemically pure, i.e., 99.5% with less than 0.5% of chemical impurities with optical purity greater than 99%.

By using (R)-camphorsulfonic acid in step E and step F, the process may be modified to produce the R,R/S,R-racemic diastereomeric acid addition salt of formula XIV in step E (Example 6) and the R,R-diastereomeric acid addition salt of (R)-CSA of formula XV in step F (Example 7) and the R-enantiomer of the compound of formula I in step G (Example 8).

Description of an alternative conventional process for resolution of diasteremeric (S)-camphorsulfonic acid salts XII The process of the present invention also contemplates that the composition of formula XI may also be resolved to afford the substantially optically pure S,S-diastereomer of formula XII by means of a crystallization process in ethanol. This process advantageously avoids the use of methylene chloride and DMF. Furthermore, the mother liquors which contain mostly the undesired R,S-diastereomer of formula XIII may be advantageously recycled by racemization to desired S,S-diastereomeric compound of formula XII under acidic conditions thus avoiding the formation of the free base of formula Z and the need to reform the (S)-CSA acid salt of formula XI. The compound of formula XI generated by racemization is then re-resolved as described hereinabove to afford additional quantities of XII.

The compound of formula XI is dissolved in ethanol, preferably 95:5 (v/v) ethanol:water by heating, preferably with agitation, under an inert atmosphere such as nitrogen or argon. The amount of ethanol should be in the range of 25 to 35 volumes, preferably about 30 volumes. When complete solution is achieved, the solution is allowed to cool to about 15 to 25 C., preferably to about 20 C. and held at this temperature for 1 to 24 hours, preferably about 6 hours. The compound of formula XII is isolated by filtration and washed with ethanol.

Preferably about 0.5 to about 0.7 equivalents of (S)-camphorsulfonic acid is added to the mother liquors which contain mostly the R,S-diastereomer acid addition salt. These mother liquors are heated at between 50 C. and reflux temperature, preferably about reflux temperature until racemization is complete. The S,S/R,S ratio achieved in compound of the formula XI is usually about 47:53. The concentration of compound of formula XI in the ethanol is adjusted to about from 100 g/L to about 30 g/L preferably about 60 g/L by concentration at atmospheric pressure or optionally by adding an additional amount of the acid addition salt of formula XI. The heating is preferably carried out with agitation under an inert atmosphere such as nitrogen or argon. After achieving the desired concentration of the compound of formula XI, the solution is allowed to cool as before to about 15 to 25 C., preferably about 20 C. and held at this temperature for 1 to 24 hours, preferably about 6 hours. The desired S,S-compound of formula XII is isolated by filtration and washed with ethanol. The mother liquors may be recycled as described hereinabove.

EXAMPLE 1 (STEP A)

Preparation of 2'-Hydroxy-4'-tetrahydropyranyloxy-2-(4"-tetrahydropyranyloxyphenyl)acetophenone

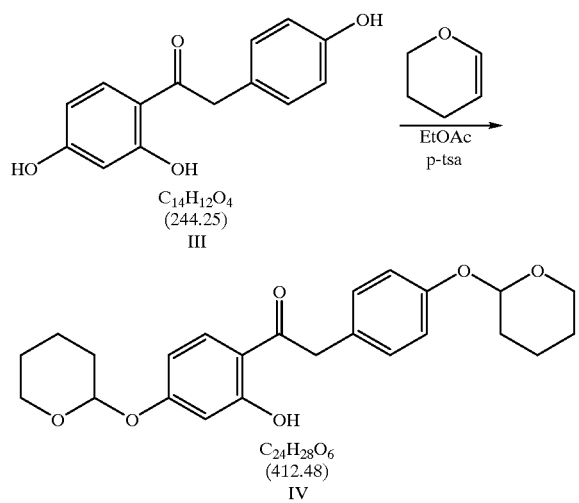

Procedure

1. To a 500 mL 3-necked round bottomed flask fitted with a mechanical stirer, thermometer, nitrogen inlet and condenser, charge the 2',4'-dihydroxy-2-(4"-hydroxyphenyl)acetophenone (48.85 g, 0.2 mole) 3,4-dihydropyran (Aldrich, 91.24 mL, 1.0 mole) and ethyl acetate (Fisher, 90 mL).

2. Add the p-toluenesulfonic acid monohydrate "p-tsa" (MCB, 30.4 mg, 0.16 mmole) and blanket the reaction with nitrogen. There is an exothermic reaction and the temperature rises from 21 C. to about 55 C. in about 5 minutes.

3. Stir the reaction for about 3 hours until the conversion of starting material into product is completed. The course of the reaction may be followed by TLC or HPLC.

4. When the reaction is complete, charge the triethylamine (Aldrich, 1.4 mL, 0.01 mole) to the reaction mixture.

5. Concentrate the so-formed mixture under reduced pressure and keep the internal temperature at 65 C. until no more volatiles are collected. 6. When the distillation is complete, break the partial vacuum with nitrogen and charge 350 mL of isopropanol to the residual oil.

7. Remove the heating bath, allow the so-formed solution to cool to ambient temperature with agitation; then cool the solution with an ice bath.

8. Stir the so-formed reaction mixture for about 1.5 hours and filter off the product and wash it with 250 mL of cold isopropanol until the washings are colorless.

9. Dry the product in a draft oven at 40 C. to obtain 67.9 g (82% of theory) of 2'-hydroxy-4'-tetrahydropyranyloxy-2-(4"-tetrahydropyranyloxyphenyl)-acetophenone (Purity 99% (area normalization by HPLC)

EXAMPLE 2 (STEPS B & C)

Preparation of (±)-trans 2-(4"-[2'"-piperidinoethoxy]phenyl)-3-(4'-tetrahydropyranyloxyphenyl)-7-tetrahydropyranyloxy-2,3-dihydro-4H-1-benzopyran-4-one

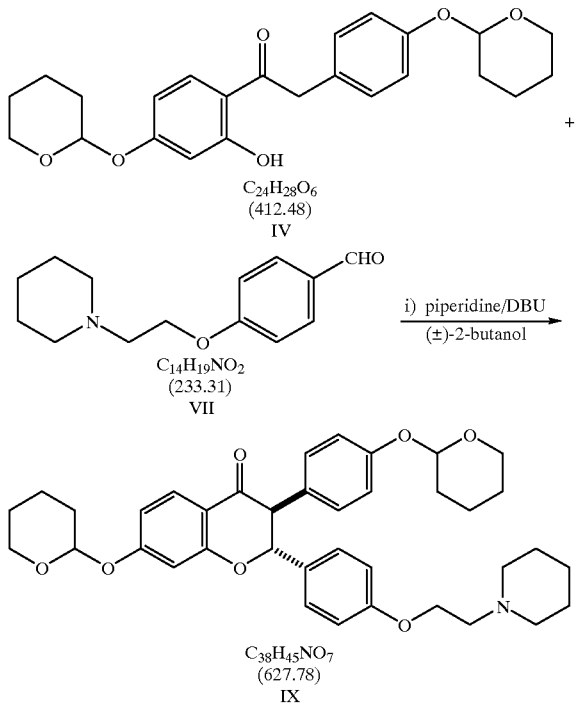

Procedure

1. To a 500 mL 3-necked round bottomed flask fitted with a mechanical stirer, thermometer, nitrogen inlet and condenser with a take off such as a Dean-Stark trap, charge the 4-(2'-piperidinoethoxy)benzaldehyde (36.75 g, 0.158 mole) and 160 mL of (±)-2-butanol (available from Fischer Scientific).
2. Add the 2'-hydroxy-4'-tetrahydropyranyloxy-(4-tetrahydropyranyloxy-phenyl)acetophenone produced in accordance with Example 1 (61.87 g, 0.15 mole), piperidine (Aldrich, 99% pure, 4.26 g, 0.05 mole) and diazabicyclo[5,4,0]undec-7-ene ("DBU") (available from Aldrich, 97%, 7.61 g, 0.05 mole) then blanket the reaction with dry nitrogen.
3. Heat the so-formed reaction mixture with agitation to reflux (98° C.) at atmospheric pressure.
4. When a gentle reflux has been achieved, slowly distil out 80 mL of (±)-2-butanol over a period of about 2 hours.
5. Continue to heat the reaction mixture at reflux temperature for about 2 more hours without further concentration. Monitor the Knoevenagel reaction by HPLC.
6. Cool the reaction mixture to 80° C. and add 200 mL of isopropanol.
7. Allow the so-formed reaction mixture to cool to between 20° C. and 25° C. Continue stirring the so-formed solution for 48 hours during which time the intermediate chalcones (the compounds of formula VIII) cyclize to the product of formula IX, (±)-trans-2-(4"-[2'"-piperidinoethoxy]phenyl)-3-(4'-tetrahydropyranyloxyphenyl)-7-tetrahydropyranyloxy-2,3-dihydro-4H-1-benzopyran-4-one which crystallizes out of solution. Seeds of the product of formula IX may be added if crystallization has not commenced after 6 hours. cis-IX also rearranges to trans-IX during this period.
8. Collect the crystals of IX by filtration and wash them with 3×90 mL portions of isopropanol.
9. Dry the crystalline product at a temperature between 40–50° C. in a draft oven to obtain 81.93 g, (86.1% of theory, corrected for purity) of the product of formula IX (Purity 98.9% by HPLC)

EXAMPLE 3 (STEPS D AND E)

Preparation of (2R,S)-7-hydroxy-3-(4'-hydroxyphenyl)-4-methyl-2-(4"-[2'"-piperidinoethoxy]phenyl)-2H-1-benzopyran (S)-(+)-camphorsulfonate

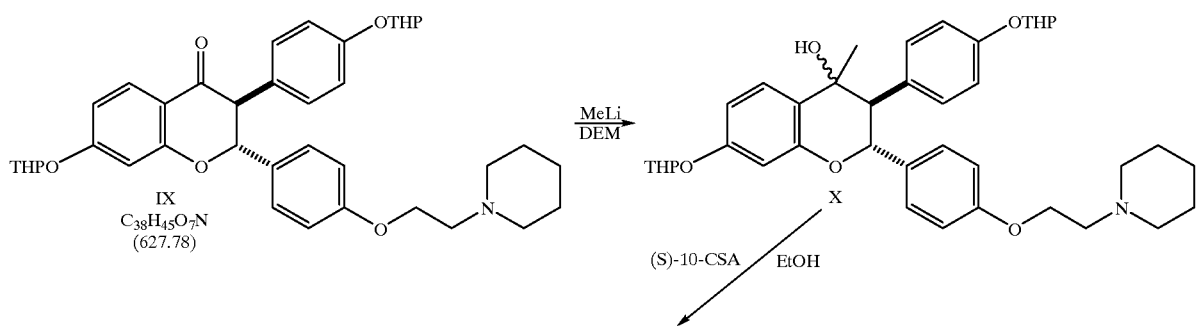

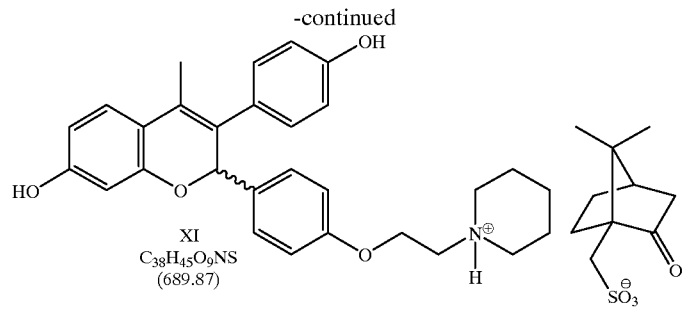

-continued

XI
C$_{38}$H$_{45}$O$_9$NS
(689.87)

Procedure

1. To a 1 L three neck, round bottomed flask fitted with a mechanical stirrer, thermometer, nitrogen inlet and addition funnel, charge the (±)-trans 2-(4"-[2'''-piperidinoethoxy]phenyl)-3-(4'-tetrahydropyranyloxyphenyl)-7-tetrahydropyranyloxy-2,3-dihydro-4H-1-benzopyran-4-one (50.0 g, 0.0796 mole) of Example 2.
2. Charge the tert-butyl methyl ether (250 mL) and blanket the reaction with dry nitrogen gas.
3. Cool the so-formed suspension to 0° C. with agitation.
4. Charge 8% methyl lithium solution in diethoxymethane (75.1 mL, 0.263 mole, 3.3 eq.) to the flask during a 30 min. period, while maintaining the temperature of the reaction mixture below 5° C.
5. Maintain the reaction mixture at 0° C. for 15 minutes, remove the cooling bath and allow the so-formed solution to warm to ambient temperature over a 45 minute period.
6. Maintain the so-formed reaction mixture for an additional 4 hours at ambient temperature and then cool the solution to 0° C. The reaction may be monitored by HPLC.
7. Charge an aqueous NH$_4$Cl solution (13.1 g in 50 mL of H$_2$O) dropwise to the reaction mixture, maintaining the so-formed reaction mixture at a temperature below 15° C.
8. Remove the cooling bath and agitate the so-formed mixture for an additional 2 min at ambient temperature.
9. Transfer the resulting clear solution into a 1 L separation funnel and separate the lower aqueous phase.
10. Wash the organic phase with 40 mL of saturated sodium chloride solution.
11. Separate the lower aqueous phase.
12. Charge the upper organic phase to a 1 L three neck round bottomed flask fitted with a stirrer, thermometer and distillation condenser.
13. Concentrate the solution to 90 mL and maintain the internal temperature below 76° C.
14. Cool the so-formed residue to ambient temperature.
15. Stir the so-formed reaction mixture and charge 50 mL of 2B ethanol (denatured with 5 volume % methanol & 5 volume % isopropanol) and the (S)-(+)-camphorsulfonic acid. (20.5 g, 0.0876 mole, 1.1 eq.)
16. Continue to stir the so-formed reaction mixture for about 15 minutes and charge 350 mL of isopropanol to the resulting yellowish thick slurry. The isopropanol should not be added until the crystallization is well underway and the slurry becomes quite thick.
17. Stir the so-formed slurry for 24 hours at about 20° C.
18. Separate the so-formed crystals by filtration under nitrogen and rinse out the flask with some of the mother liquor if necessary.
19. Wash the crystalline product with 50 mL of isopropanol.
20. Dry the crystalline product in a draft oven below 50 C. for 24 hours to give 50.7 g (90% of theory) of (2R,S)-7-hydroxy-3-(4'-hydroxyphenyl)-4-methyl-2-(4"-[2'''-piperidinoethoxy]phenyl)-2H-1-benzopyran (S)-(+)-camphorsulfonate (97.8% purity relative to a reference standard as determined by HPLC on a YMC Basic 5 column (4.6 mm×250 mm), mobile phase 10 mmolar solution of ammonium acetate in methanol/water (65:35), 1.0 mL/min flow rate, UV detection @ 240 nm, Inj. vol. 20 µL, conc. 0.4 mg/mL).

EXAMPLE 4 (STEP F)

Preparation of (2S)-7-hydroxy-3-(4'-hydroxyphenyl)-4-methyl-2-(4"-[2'''-piperidinoethoxy]phenyl)-2H-1-benzopyran (S)-(10)-camphorsulfonate,

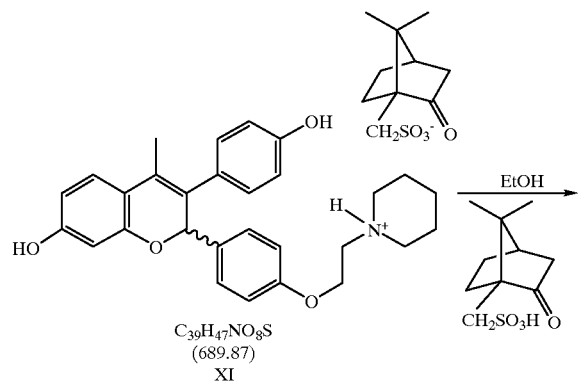

C$_{39}$H$_{47}$NO$_8$S
(689.87)
XI

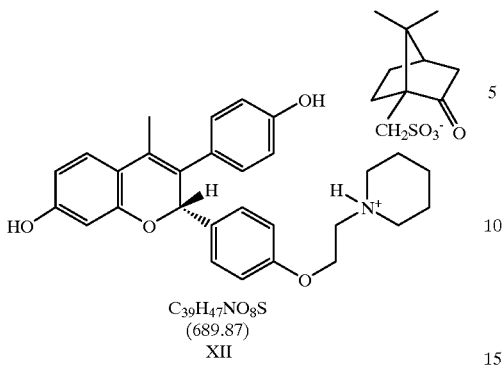

$C_{39}H_{47}NO_8S$
(689.87)
XII

Procedure
1. To a 3 necked round bottomed flask fitted with a mechanical stirrer, thermometer, condenser and nitrogen inlet charge the (2R,S)-2-(p-[2''-piperidinyl] ethoxyphenyl)-3-(4'-hydroxyphenyl)-4-methyl-7-hydroxychrom-3-ene (50 g, 0.0725 mole) from Example 3, (S)-(+)-camphorsulfonic acid (10 g, 0.043 mole) and 300 mL of 2B ethanol.
2. Blanket the flask with nitrogen and heat the suspension at 73° C. with agitation for 24 hours The diastereomer ratio may be followed by chiral HPLC (see Step 6).
3. Continue stiring the suspension and allow it to cool to room temperature over a 1 hour period.
4. Continue stirring the so-formed suspension at room temperature for 4 more hours.
5. Filter off the so-formed crystals and wash them with cold (2B) ethanol.
6. Dry the crystalline product in a draft oven at 50° C. to obtain (2S)-7-hydroxy-3-(4'-hydroxyphenyl)-4-methyl-2-(4''-[2'''-piperidinoethoxy]phenyl)-2H-1-benzopyran (S)-(+)-camphorsulfonate, 29 g, (58%), de 98% determined by chiral HPLC using the method described below.

Optical purity was determined on a Chiralpak AD column (4.6 mm×250 mm) (Daicel Chemical Industries Inc.), mobile phase: hexane/ethyl alcohol/diethyl-amine (85:15:0.1), flow rate: 1.4 mL/min, UV detection @ 240 nm, Inj. vol. 20 mL, conc. 0.5 mg/mL in the mobile phase, column temperature 26° C.

EXAMPLE 5 (STEP G)

Preparation of (S)-7-hydroxy-3-(4'-hydroxyphenyl)-4-methyl-2-(4''-[2'''-(1-piperidino)ethoxy]phenyl)-2H-benzopyran 4',7-bistrimethylacetate,

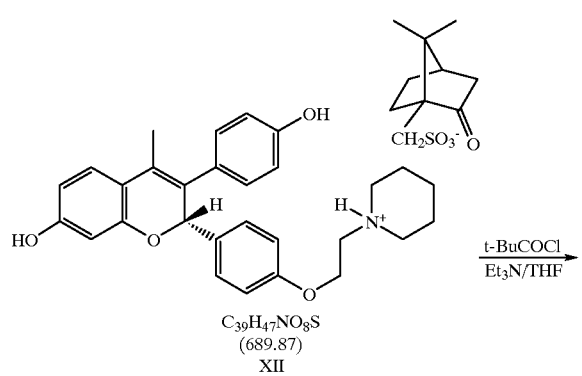

$C_{39}H_{47}NO_8S$
(689.87)
XII $C_{39}H_{47}NO_6$
(625.81)
I

Procedure
1. To a 1 L flask, charge (2S)-7-hydroxy-3-(4'-hydroxyphenyl)-4-methyl-2-(4''-[2'''-piperidinoethoxy] phenyl)-2H-1-benzopyran (S)-(+)-camphorsulfonate (20 g, 0.029 mole) from Example 4 and 60 mL of dry tetrahydrofuran.
2. Blanket the suspension with nitrogen.
3. Charge the triethylamine (Aldrich, 99% pure, 16.5 mL, 0.119 mole, 4.1 equivalents) and agitate the so-formed suspension at between 15° and 25° C. for about 10 minutes until complete solution is achieved.
4. Cool the so-formed reaction mixture to a temperature between −20° and −15° C.
5. Charge a solution of the trimethylacetyl chloride ("t-BuCOCl"), (Aldrich, 99% pure, 10.14 g, 0.084 mole, 2.9 equivalents) in 20 mL of dry tetrahydrofuran at a rate such that the temperature of the so-formed reaction mixture does not exceed −10° C.
6. Maintain the temperature of the so-formed reaction mixture between −15° and −10° C. for 15 minutes and then allow the reaction mixture to reach a temperature of 0 to −5° C. over a 1 hour period.
7. Maintain the reaction mixture at this temperature until the reaction is complete. The reaction is complete in about 1.5 hours and may be monitored by HPLC (YMC Basic S-5 colum) or TLC. (Analtec silica gel GF 250 m, methylene chloride/methanol/ammonia 19 ml: 1 ml : 4 drops. Visualize with iodine).
8. Charge to the reaction mixture 80 mL of t-butyl methyl ether and a solution of sodium bicarbonate (7.5 g in 150 mL water) and agitate the so-formed mixture for 15 minutes at room temperature to destroy the excess trimethylacetyl chloride.
9. Separate the phases and wash the upper organic layer with a solution of 7.5 g of sodium chloride in 150 mL of water.
10. Separate the phases and transfer the upper organic layer to a flask fitted with a distillation condenser.
11. Charge 180 mL of isopropanol to the flask and concentrate the so-formed solution by atmospheric distillation.
12. Charge an additional 170 ml isopropanol (as space in the flask permits) and continue to concentrate the solution to a final volume of about 320 mL.
13. Charge the Darco and Supercel to the flask and reflux the so-formed mixture for 15 minutes. Filter the mixture. This should be done quickly to avoid crystallization on the filter.
14. Wash the Darco and Supercel on the filter with fresh isopropanol.
15. Combine the filtrate and washings and concentrate the combination to a final volume of 320 mL. The final volume is important to ensure adequate purity, ee and yield. Either concentrate solution at 1 atmosphere or add isopropanol to achieve this final volume.

16. Filter off the product and wash with 40 mL cold (0–5° C.) isopropanol and then with 108 mL of heptanes (available from Fisher Scientific).

17. Dry the crystalline product at 600–70° C. in a draft oven for 12 hours to obtain 15 g (83% yield, 99% purity) of the compound of formula I, i.e., (S)-7-hydroxy-3-(4'-hydroxy-phenyl)-4-methyl-2-(4''-[2'''-(1-piperidino)ethoxy]phenyl)-2H-benzopyran 4',7-bistrimethylacetate (99% chemical purity by HPLC YMC Basic S-5 column (4.6 mm×250 mm), mobile phase: 10 mmolar solution of ammonium acetate in methanol/water (85:15), flow rate: 1.0 ml/min, UV detection @ 240 nm, Inj. vol. 10 mL, conc. 1 mg/mL).

EXAMPLE 6

Preparation of (2R,S)-7-hydroxy-3-(4'-hydroxyphenyl)-4-methyl-2-(4''-[2'''-piperidinoethoxy]phenyl)-2H-1-benzopyran (R)-(10)-camphorsulfonate 5. After 15 minutes at 0° C., remove the cooling bath and allow the solution to warm to ambient temperature over a 45 minute period.

6. After an additional 4 hours at ambient temperature, cool the solution to 0° C.

7. Charge the saturated aqueous $NH_4Cl$ solution (666 mL) dropwise, maintaining the temperature below 15° C.

8. Remove the cooling bath and agitate the batch for an additional 2 min at ambient temperature.

9. Separate the lower aqueous phase.

10 Wash the organic phase with 666 mL saturated sodium chloride solution.

11. Separate the lower aqueous phase.

12. Concentrate the upper organic phase to about 1.2 L.

13. Cool the residue to ambient temperature.

14. With agitation, charge 2.0 L of EtOH (denatured with 5% MeOH and 5% i-PrOH) and (R)-10-camphorsulfonic acid (277 g, 1.19 mole).

15. After about 15 min, charge isopropanol (2.66 L) to the resulting yellowish thick slurry.

16. Agitate the slurry for 48 h at about 20° C.

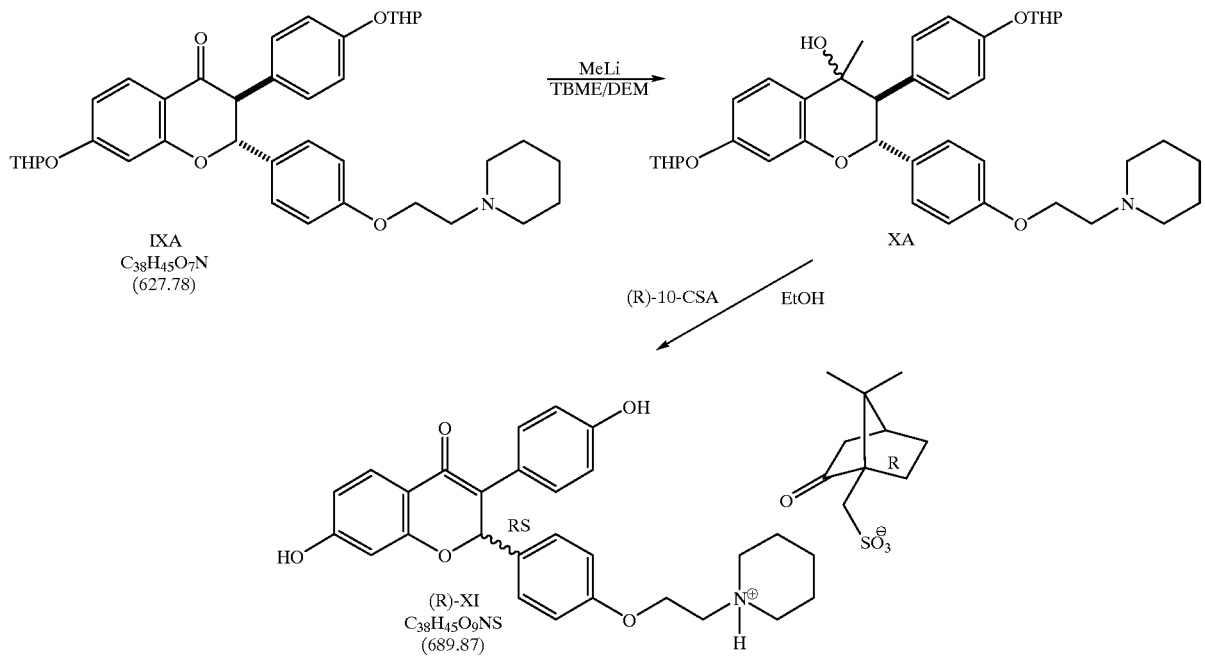

Procedure

1. To a 12 L three neck, round bottomed flask fitted with a mechanical stirrer, thermometer, nitrogen inlet and addition funnel, charge the (±)-trans 2-(4''-[2'''-piperidinoethoxy]-phenyl)-3-(4'-tetrahydropyranyloxyphenyl)-7-tetrahydropyranyloxy-2,3-dihydro-4H-1-benzopyran-4-one (666.3 g, 1.06 mole) of example 2.

2. Charge the tert-butyl methyl ether (4 L) and blanket the flask with nitrogen.

3. Cool the suspension to 0° C. with agitation.

4. Charge the methyllithium (8% solution in diethoxymethane, 1.0 L) to the flask in a 30 min period, maintaining the temperature below 5° C.

17. Separate the crystals by filtration under nitrogen and rinse out the flask with some of the mother liquor if neccessary.

18. Wash the product with isopropanol.

19. Dry the (2R,S)-7-hydroxy-3-(4'-hydroxyphenyl)-4-methyl-2-(4''-[2'''-piperidinoethoxy]-phenyl)-2H-1-benzopyran (R)-(10)-camphorsulfonate in a draft oven below 50° C. for 24 h to give 647 g, Purity 97.4%, Yield 88% (86% corrected for purity).

Purity measured by HPLC using a YMC Basic column S-5 micron, (4.6×250 mm). Mobile phase; 10 mmolar solution of ammonium acetate in methanol/water (65:35); Flow rate, 1.0 ml/min; injection volume, 20 L; Concentration, 0.4 mg/ml in MeOH; UV detection @ 240 nm.

EXAMPLE 7

Preparation of (2R)-7-hydroxy-3-(4'-hydroxyphenyl)-4-methyl-2-(4"-[2"'-piperidinoethoxy]phenyl)-2H-1-benzopyran (R)-(10)-camphorsulfonate

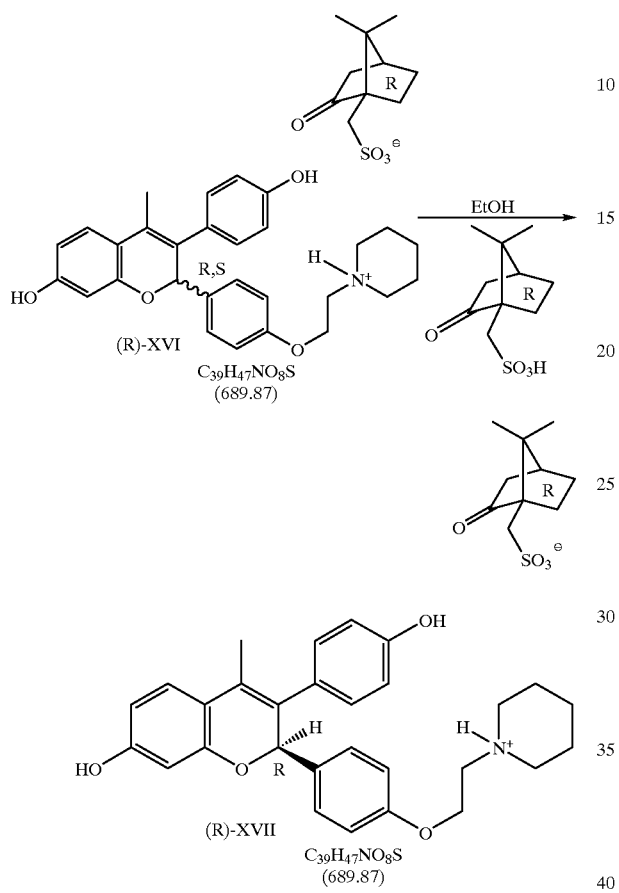

Procedure

1. To a 12 L, 3 necked round bottomed flask fitted with a mechanical stirrer, thermometer, condenser and nitogen inlet charge the (2R,S)-2-(p-[2'-piperidinyl] ethoxyphenyl)-3-(4'-hydroxyphenyl)-4-methyl-7-hydroxychrom-3-ene (R)-(10)-camphorsulfonic acid salt (compound of Example 6) (630 g, 0.913 mole), (R)-(−)-camphorsulfonic acid (12.8 g, 0.054 mole) and 2B(190 Proof) ethyl alcohol (2.55 L).
2. Blanket the flask with nitrogen and heat the suspension at 73° C. (internal temperature) with agitation for 24 hours.
3. Continue stirring and allow the solution to cool to 12° C. over 1 hour.
4. Continue stirring for 4 more hours.
5. Filter off the crystals and wash with cold 200 proof ethanol.
6. Dry the product in a draft oven at 50° C. to obtain 375.8 g, (60 % yield), de 98%. of (R)-2-(p-[2"-piperidinyl] ethoxyphenyl)-3-(4'-hydroxyphenyl)-4-methyl-7-hydroxychrom-3-ene (1R)-(10)-camphorsulphonic acid salt.

YMC Basic column S-5 micron, (4.6×250 mm). Mobile phase; 10 mmolar solution of ammonium acetate in methanol/water (65:35); Flow rate, 1.0 ml/min; Injection volume, 20 mL; Concentration, 0.4 mg/ml in MeOH; UV detection @ 240 nm.

Optical purity was measured by HPLC using a Chiralpak AD column (250 mm×4.6 mm) (Daicel Chemical Industries Inc.), mobile phase:hexanes:ethanol:diethylamine (85:15:0.1), flow rate: 1.4 mL/min, UV detection @ 240 nm, Inj. vol. 20 mL, conc. 0.5 mg/mL in mobile phase, column temperature 26° C.

EXAMPLE 8

Preparation of (R)-7-hydroxy-3-(4'-hydroxyphenyl)-4-methyl-2-(4"-[2"'-(1-piperidino)ethoxy]phenyl)-2H-benzopyran 4',7-bistrimethylacetate

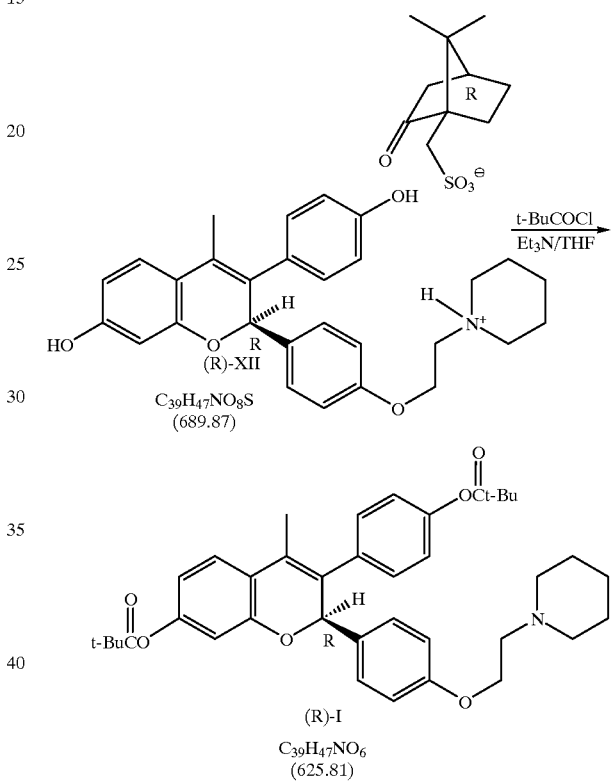

Procedure

1. To a 5 L, 3-necked flask, charge (2R)-7-hydroxy-3-(4'-hydroxyphenyl)-4-methyl-2-(4"-[2"'-piperidinoethoxy] phenyl)-2H-1-benzopyran (S)-(10)-camphorsulfonate (compound of example 7) (370 g, 0.536 mole) anhydrous tetrahydrofuran (1.4 L).
2. Blanket the suspension with nitrogen.
3. Charge the triethylamine (310 ml, 0.222 mole) and agitate the suspension at between 15° and 25° C. for about 10 minutes until complete solution is achieved.
4. Cool the mixture to between −20° and −15° C.
5. Charge a solution of the trimethylacetyl chloride (195.8 g, 0.162 mole) in anhydrous tetrahydrofuran (370 mL) at a rate such that the reaction temperature does not exceed −10° C.
6. Maintain the temperature between −15° and −10° C. for 15 minutes then allow the batch to reach 0° to −5° C. over 1 hour.
7. Maintain this temperature until the reaction is complete.

29

8. Charge 80 mL t-butylmethylether (1.5 L) and a solution of sodium bicarbonate (141 g in 2.25 L water) and agitate the batch for 15 minutes at room temperature.
9. Separate the phases and wash the upper organic layer with a solution of sodium chloride (141 g in 2.25 L water).
10. Separate the phases and transfer the upper organic layer to a flask fitted with distillation condenser.
11. Charge isopropanol (3.5 L) and concentrate the solution by atmospheric distillation.
12. As room permits, charge an additional isopropanol (3.0 L) and continue to concentrate the solution to a final volume of about 6.0 L.
13. Charge the Darco (37 g) and Supercel (37 g) and reflux for 15 minutes.
14. Filter off the Darco and Supercel and wash them with hot isopropanol (1.0 L).
15. Combine the filtrate and washings and concentrate to a final volume of about 6.0 L.
16. With agitation allow the batch to cool and crystallize overnight.
17. Filter off the product and wash with cold isopropanol.
18. Dry the batch at 60° C. in a vacuum oven. Yield of (R)-7-hydroxy-3-(4'-hydroxyphenyl)-4-methyl-2-(4"-[2'''-(1-piperidino)ethoxy]phenyl)-2H-benzopyran 4',7-bistrimethylacetate 294 g (88% yield, 99% ee, 99% purity).

Chemical purity measured HPLC using YMC Basic S-5 micron column (4.6 mm×250 mm), mobile phase: 10 mmolar solution of ammonium acetate in methanol/water (85:15), flow rate: 1.0 mL/min, UV detection @ 240 nm, lnj. vol. 10 L, conc. 1 mg/mL.

Optical purity measured by HPLC using a Chiralpak AD column (250 mm×4.6 mm) (Daicel Chemical Industries Inc.), mobile phase:hexanes:ethanol:isopropanol:diethylamine (95:3:2:0.1), flow rate: 1.0 mL/min, UV detection @ 240 nm, Inj. vol. 10 L, conc. 2 mg/mL in mobile phase, column temperature 26° C.

EXAMPLE 9

Preparation of (2S)-7-hydroxy-3-(4'-hydroxyphenyl)-4-methyl-2-(4"-[2'''-piperidinoethoxy]phenyl)-2H-1-benzopyran (S)-(10)-camphorsulfonate

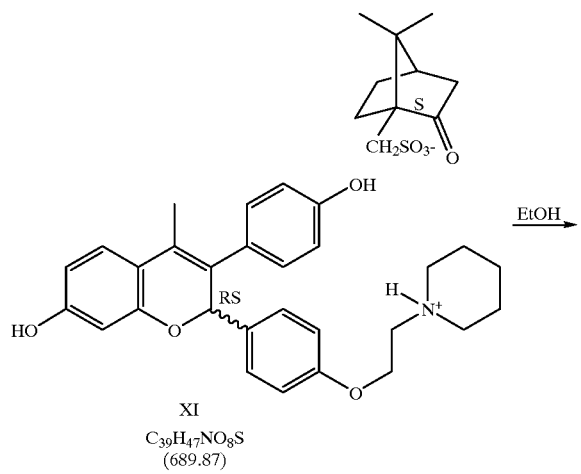

XI
$C_{39}H_{47}NO_8S$
(689.87)

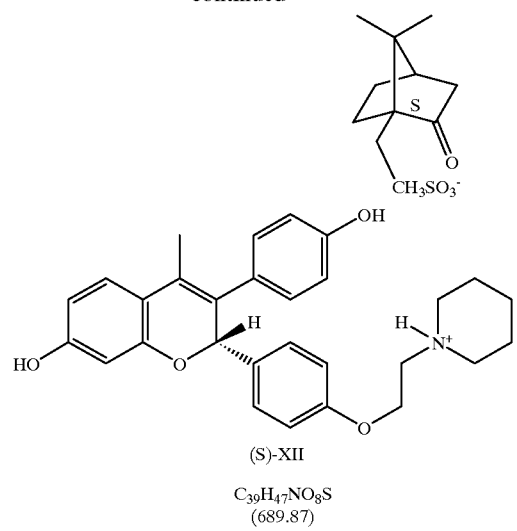

(S)-XII
$C_{39}H_{47}NO_8S$
(689.87)

Procedure

1. To a 2 L Erhlenmeyer flask fitted with a magnetic stirring bar, charge the (2R,S)-7-hydroxy-3-(4'-hydroxyphenyl)-4-methyl-2-(4"-[2'''-piperidinoethoxy]phenyl)-2H-1-benzopyran (S)-(10)-camphorsulfonate (compound of example 3) (25 g, 0.072 mole) and 190 proof ethanol (750 mL).
2. Agitate and heat the suspension until a clear solution is obtained.
3. Remove the heat source and continue stiring allowing the solution to cool room temperature.
4. If neccessary, seed with crystals of (2S)-7-hydroxy-3-(4'-hydroxyphenyl)-4-methyl-2-(4"-[2'''-piperidinoethoxy]phenyl)-2H-1-benzopyran (S)-(10)-camphorsulfonate.
5. Continue stirring for 24 hours at ambient temperature.
6. Filter off the crystals and wash with cold 190 proof ethanol.
7. Dry the product in a draft oven at 50° C. Yield of (2S)-7-hydroxy-3-(4'-hydroxyphenyl)-4-methyl-2-(4"-[2'''-piperidinoethoxy]phenyl)-2H-1-benzopyran (S)-(10)-camphorsulfonate, 9.89 g, (39.6%, corrected for purity); Purity 96.5%, de 96.6%

The purity was determined using the following HPLC system: YMC Basic column S-5, (4.6×250 mm). Mobile phase; 10 mmolar solution of ammonium acetate in methano/water (65:35); Flow rate, 1.0 ml/min; Injection volume, 20 μL; Concentration, 0.4 mg/ml in MeOH; UV detection @ 240 nm.

Optical purity measured by HPLC using a Chiralpak AD column (250 mm×4.6 mm) (Daicel Chemical Industries Inc.), mobile phase:hexanes:ethanol:diethylamine (85:15:0.1), flow rate: 1.4 mL/min, UV detection @ 240 nm, Inj. vol. 20 μL, conc. 0.5 mg/mL in mobile phase, column temperature 26° C.

EXAMPLE 10

Preparation of 2-(S)-7-hydroxy-3-(4'-hydroxyphenyl)-4-methyl-2-(4"-[2'"-piperidinoethoxy]phenyl)-2H-1-benzopyran (S)-(10)-camphorsulfonate from mother liqors containing 2-(R)-7-hydroxy-3-(4'-hydroxyphenyl)-4-methyl-2-(4"-[2'"-piperidinoethoxy]phenyl)-2H-1-benzopyran (S)-(10)-camphorsulfonate

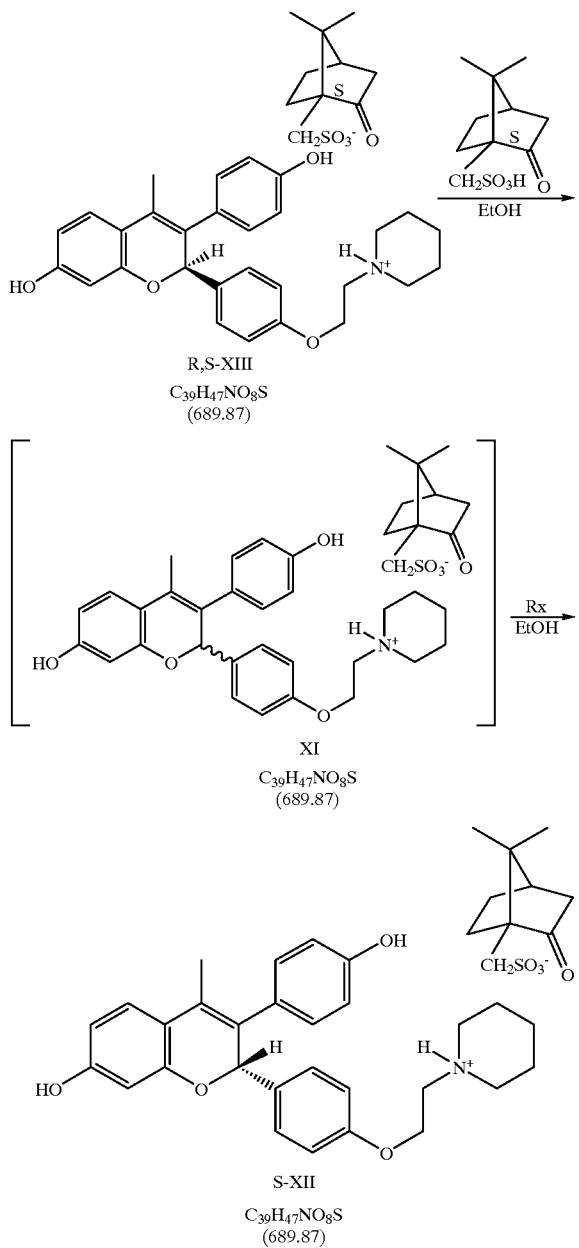

Procedure

1. Add (S)-(10)-camphorsulfonic acid (0.25 g) to the mother liquors and washes from example 9 and concentrate the solution by slow distillation at atmosheric pressure under nitrogen to about 225 ml.
2. Continue to agitate and reflux the solution until the ratio of diastereomeric camphorsulfonic acid salts is about 47:53 (S,S:R,S).
3. Remove the heat source and continue stiring allowing the solution to cool room temperature.
4. If neccessary, seed with crystals of (2S)-7-hydroxy-3-(4'-hydroxyphenyl)-4-methyl-2-(4"-[2'"-piperidinoethoxy]phenyl)-2H-1-benzopyran (S)-(10)-camphorsulfonate.
5. Continue stirring for 24 hours at ambient temperature.
6. Filter off the crystals and wash with cold 190 proof ethanol.
7. Dry the product in a draft oven at 50° C. Yield of (2S)-7-hydroxy-3-(4'-hydroxyphenyl)-4-methyl-2-(4"-[2'"-piperidinoethoxy]phenyl)-2H-1-benzopyran (S)-(10)-camphorsulfonate, 3.6 g, (24%); Purity 95%, de 96%

The purity was determined using the following HPLC system: YMC Basic column S-5, (4.6×250 mm). Mobile phase; 10 mmolar solution of ammonium acetate in methanol/water (65:35); Flow rate, 1.0 ml/min; Injection volume, 20 μL; Concentration, 0.4 mg/ml in MeOH; UV detection @ 240 nm.

Diastereomer ratio measured by HPLC using a Chiralpak AD column (250 mm×4.6 mm) (Daicel Chemical Industries Inc.), mobile phase:hexanes:ethanol:diethylamine (85:15:0.1), flow rate: 1.4 mL/min, UV detection @ 240 nm, Inj. vol. 20 μL, conc. 0.5 mg/mL in mobile phase, column temperature 26° C.

EXAMPLE 11

Synthesis of (2S)-7-Hydroxy-3-(4'-hydroxyphenyl)-4-methyl-2-(4"-[2"-piperidino]ethoxy)phenyl)-2H-benzopyran Hydrochloride (XV)

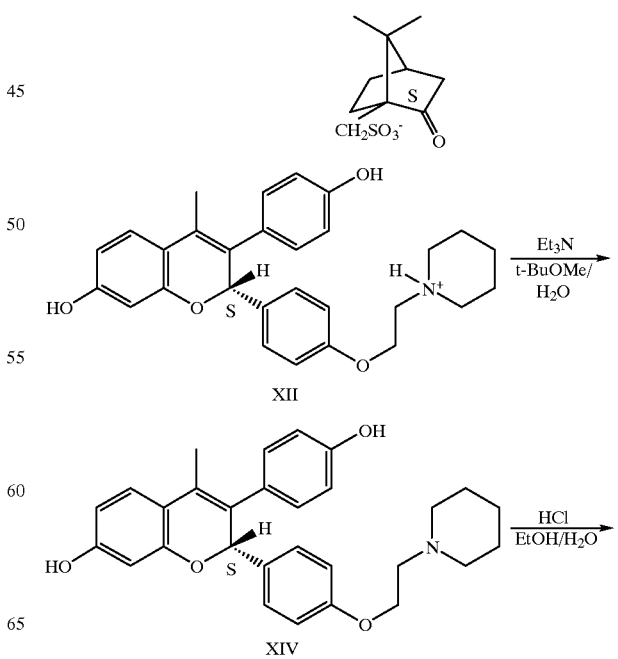

33

-continued

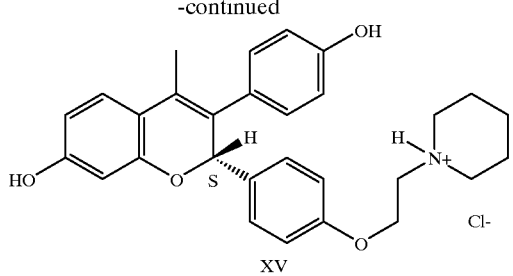

XV

A. Preparation of Compound XV

To a suspension of (2S)-7-hydroxy-3-(4'-hydroxyphenyl)-4 methyl-2-(4"-[2"'-piperidino]ethoxy)phenyl)-2H-benzopyran (1S)-10-camphorsulphonic acid salt (Compound XII) (400 g) in t-butylmethylether (5.5 L) and sterile water for injection (3.5 L) at ambient temperature was added triethylamine (114 mL). The mixture was agitated until complete solution occurred. The lower aqueous layer was separated and extracted with t-butylmethytlether (1.5 L). The t-butylmethy-lether layers were combined and washed with brine (2 L), and then concentrated under reduced pressure to 2 L and filtered through silica gel (1 50 g); the silica gel was then washed with t-butylmethylether (1.5 L). The filtrate and washings containing (2S)-7-hydroxy-3-(4-hydroxyphenyl)-4-methyl-2-(4"-[2"'-piperidino]-ethoxy)phenyl)-2H-benzopyran (Compound XIV) were combined and the solvent replaced with ethanol (190 proof, USP) (1.7 L).

To this solution, cooled to about 5° C., was added slowly with agitation over 30 minutes 2N HCL (320 ml). Agitation was continued for 30 minutes and then sterile water for injection (4.5 L) was added. Agitation was continued for a further 2 hours during which time the temperature was maintained at about 5° to 10° C. The crystals of product (XV) were filtered off, washed with sterile water for injection (1.0 L). and dried at room temperature under vacuum with a slow nitrogen flow. The yield of (2S)-7-hydroxy-3-(4'-hydroxyphenyl)-4-methyl-2-(4"-[2"'-piperidino]ethoxy)phenyl)-2H-benzopyran hydrochloride (Compound XV) was 244 g (85%).

B. Recrystallization of Compound XV (2S)-7-hydroxy-3-(4'-hydroxyphenyl)-4-methyl-2-(4-methyl-2(4"-[2"piperidino]ethoxy)phenyl)-2H-benzopyran hydrochloride (Compound XV) (4 g) was dissolved in refluxing 190 proof ethanol (40 ml). The solution was cooled to ambient temperature over and water (160 ml) was added. The mixture was filtered and the purified Compound XV dried at room temperature under vacuum with a slow nitrogen flow. Yield 3.28 g (82%).

Isocratic HPLC Assay for Chemical Purity of Compound XV

| Mobile phase: | 10 mM ammonium acetate in methanol/water (65:35). |
|---|---|
| Column | YMC basic 5 mm 120 A (4.6 mm × 250 mm) maintained at 30° C. |
| Flow Rate | 1.0 mL/min. |
| Injection vol.: | 10 mL. |
| Sample preparation | 0.5 mg/mL |
| Detector | 240 nm. |

34

HPLC Assay for Optical Purity (+)-XIV and the (−)-R-enantiomer of XIV

| Mobile phase: | hexane/ethyl alcohol/diethylamine (80:20:0.2, v/v/v). |
|---|---|
| Column | Chiralpak AD (4.6 mm × 250 mm) (Daicel Chemical Industries Inc.) |
| Flow rate: | 1.0 mL/min. |
| Injection vol.: | 20 mL |
| Sample preparation: | 0.5 mg/mL |
| Detector | 240 nm. |
| Compound | Typical retention time |
| (+)-XIV (S-enantiomer) | 7.7 minutes |
| (−)-R-enantiomer of XIV | 9.2 minutes |

In a similar manner, the R-enantiomer of Compound XV may be prepared from Compound XVII OF EXAMPLE 7.

What is claimed is:

1. A process which comprises reacting the compound of formula IV with the compound represented by formula VII

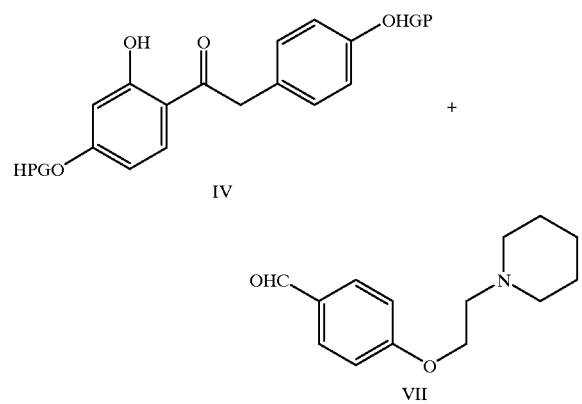

in the presence of piperidine, a hindered organic amine base and a ($C_3$–$C_6$) alkanol at temperature and for a time sufficient to produce the compound of formula IX substantially chemically pure and essentially free of the cis-isomer of the compound of formula IX and substantially free of E & Z chalcones of formula VIII, wherein HPG is an acid-labile phenolic hydroxyl protecting group:

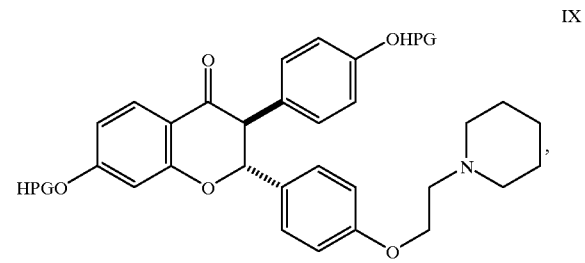

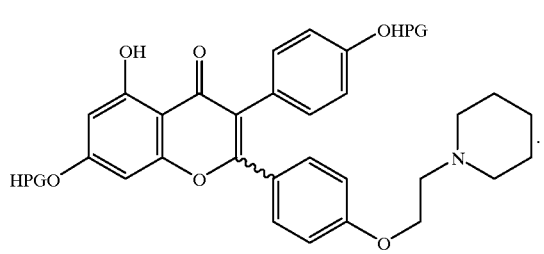

VIII

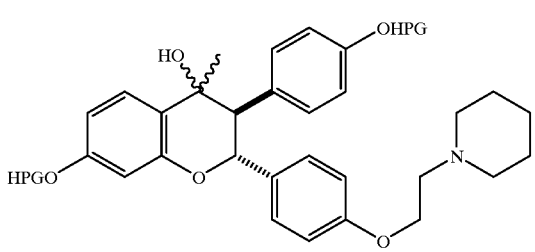

X

2. The process of claim 1 wherein the ($C_3$–$C_6$) alkanol is 2-butanol, isopropanol or isobutanol.

3. The process of claim 1 wherein the hindered organic amine base is 1,8-diazabicyclo[5,4,0]undec-7-ene, or 1,5-diazabicyclo[4.3.0]non-5-ene.

4. The process of claim 1 wherein (a) the compound of formula IV is contacted with the compound of formula VII in the presence of piperidine, and 2-butanol at the boiling point of 2-butanol for a time sufficient to substantially completely distill an azetropic mixture of 2-butanol and water to form a reaction product comprising a mixture of the E and Z chalcones of formulas VIII and cis and trans IX, and (b) the reaction mixture is cooled to a temperature in the range of about 20–25° C. and the hindered organic amino base, 1,8-diazabicyclo[5,4,0]undec-7-ene, is added and the contacting is continued for a time sufficient to produce the compound of formula IX substantially free of the E and Z chalcones of formula VIII and essentially free of the cis-isomer of the compound of formula IX:

IX

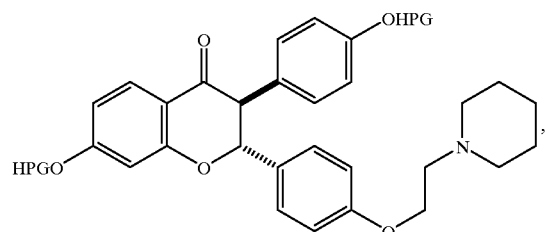

VIII

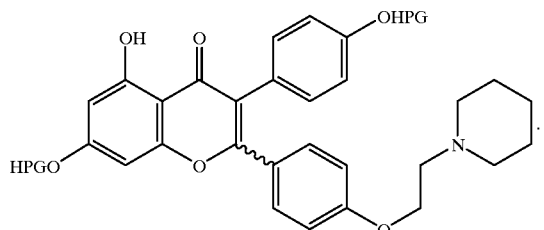

5. The process of claim 1 wherein the acid labile phenolic hydroxyl protecting group is tetrahydropyranyl.

6. The process of claim 1 which further comprises the step of reacting the compound of formula IX with a stoichiometric excess of methyl lithium in an anhydrous acyclic ether as solvent for a time and temperature sufficient to produce the compound of formula X:

7. The process of claim 6 which further comprises contacting the compound of formula X with a stoichiometric excess of (S)-(+)-camphorsulfonic and in a solvent comprising ethanol for a time and at a temperature sufficient to produce R,S/S,S-diastereometric acid addition salt of the formula XI:

XI

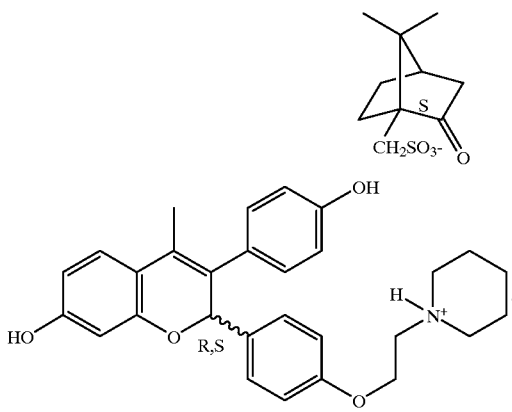

8. The process of claim 7 which further comprises contacting the diastereometric acid addition salt of the formula XI with a catalytic amount of (S)-(+) camphorsulfonic and in a solvent comprising ethanol for a time and at a temperature sufficient to produce S,S-diastereometric salt of the formula XII, substantially free of the R,S-diastereomeric acid addition salt of the formula XIII:

XII

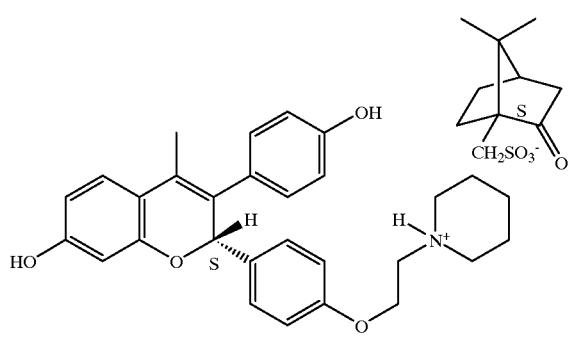

-continued

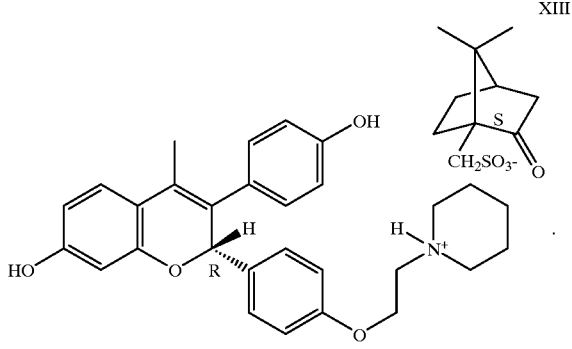

XIII

9. The process of claim 8 which further comprises contacting the the S,S-diastereometric acid addition salt of compound XII with a stoichiometric excess of pivaloyl chloride in the presence of tertiary organic amine at temperature and time sufficient to produce the compound of formula I:

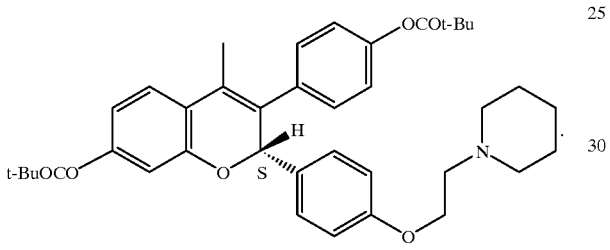

I

10. The process of claim 8 which further comprises contacting the S,S-diastereometric acid addition salt of compound XII with an amount of a tertiary organic amine at a temperature and time sufficient to produce the compound of formula XIV:

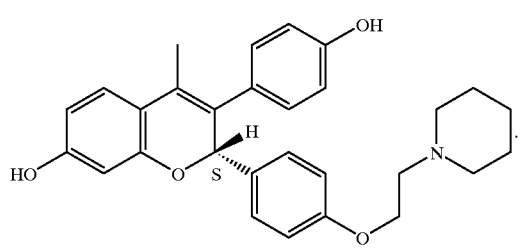

XIV

11. The process of claim 9 wherein the tertiary organic amine is tri($C_1$–$C_6$) alkylamine, pyridine or N-methylmorpholine.
12. The process of claim 10 wherein the tertiary organic amine is tri($C_1$–$C_6$) alkylamine, pyridine or N-methylmorpholine.
13. The process of claim 9 wherein the tertiary organic amine is triethylamine.
14. The process of claim 10 wherein the tertiary organic amine is triethylamine.
15. The process of claim 9 wherein a suspension the diastereomeric acid addition salt of formula XII in the acetonitrile or THF at a temperature in the range of about −20° to 20° C. is contacted with triethylamine and a stoichiometric excess of pivaloyl chloride for a time sufficient to produce the compound of formula I:

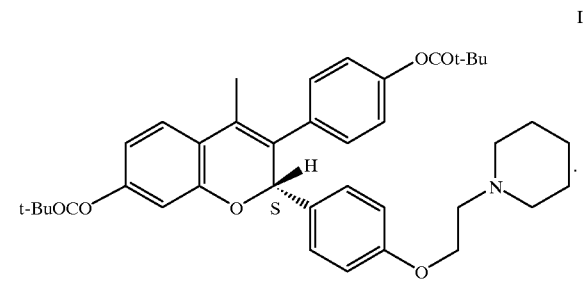

I

16. A process which comprises the steps of:
(a). reacting the compound of formula IV with the compound represented by formula VII

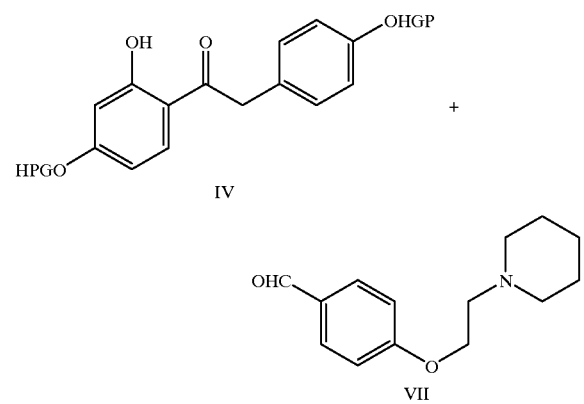

in the presence of piperidine, a hindered organic amine base and a ($C_3$–$C_6$) alkanol at temperature and for a time sufficient to produce the compound of formula IX essentially free of the cis-isomer of the compound of formula IX and substantially free of the E and Z chalcones of formula VIII, wherein HPG is an acid labile phenolic hydroxyl protecting group;

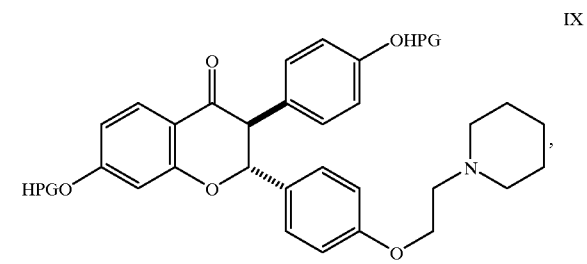

IX

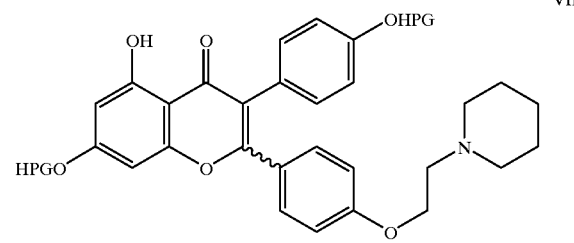

VIII (b). reacting the compound of formula IX with a stoichiometric excess of methyl lithium in an anhydrous acyclic ether or aromatic hydrocarbon solvent for a time and temperature sufficient to produce the compound of formula X;

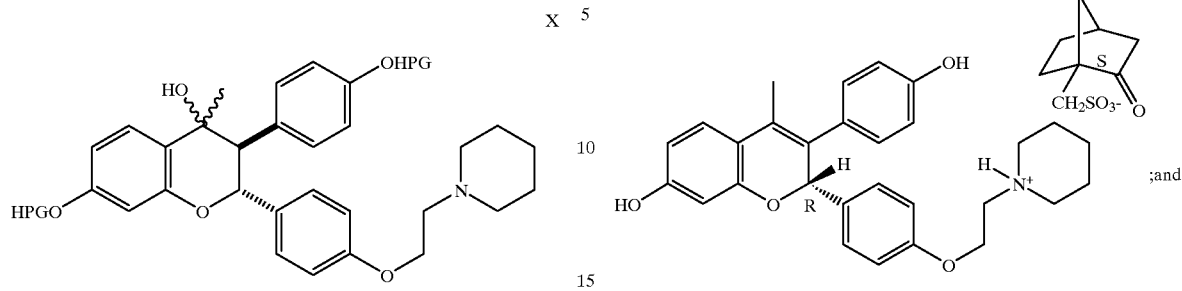

c). contacting the compound of formula X with a stoichiometric excess of (S)-(+)-camphorsulfonic and in a solvent comprising ethanol for a time and at a temperature sufficient to produce racemic R,S/S,S-acid addition salt of the formula XI;

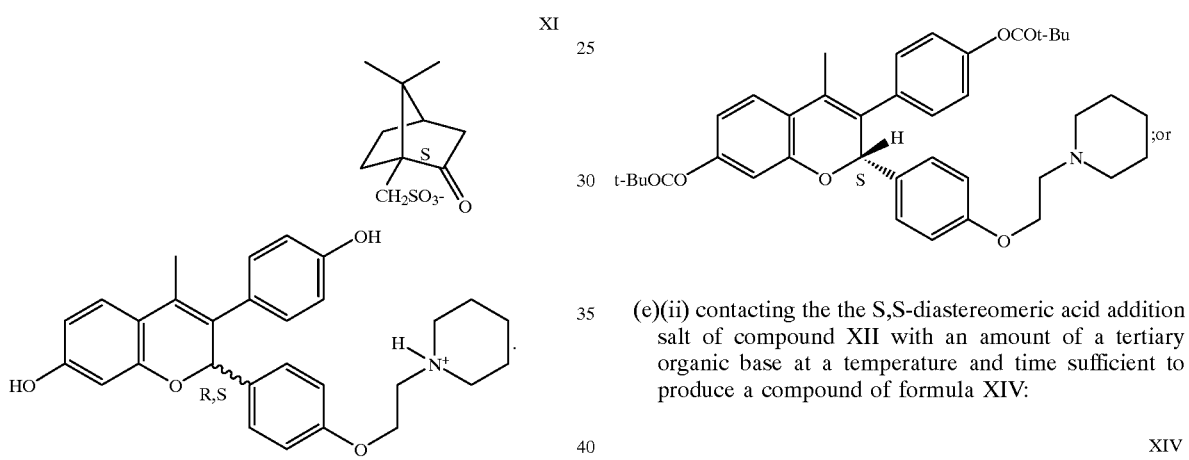

(d). contacting the racemic R,S/S,S acid addition salt of the formula XI with a catalytic amount of (S)-(+)-camphorsulfonic and in a solvent comprising ethanol for a time and at a temperature sufficient to produce a single S,S-diastereometric acid addition salt of the formula XII;

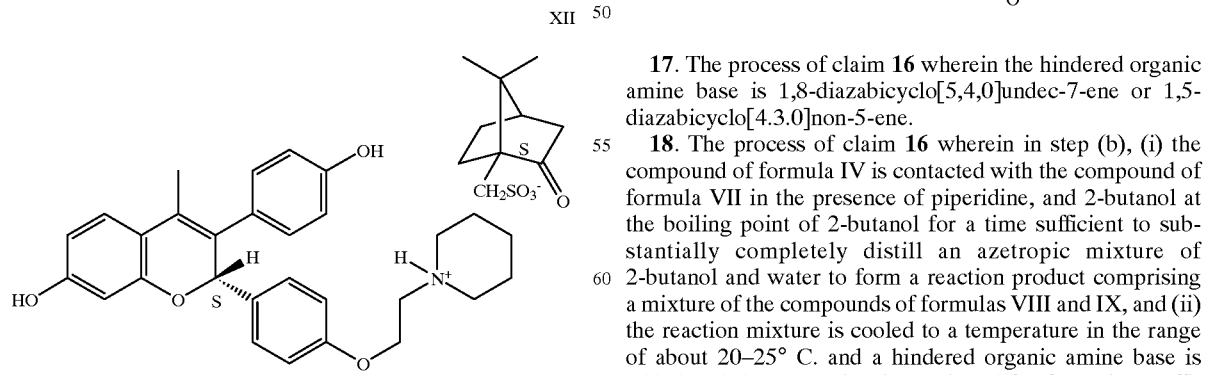

substantially free of the opposite R.S-diastereomeric acid addition salt of the formula XIII:

(e)(i) contacting the the S,S-diastereomeric acid addition salt of compound XII with a stoichiometric excess of pivaloyl chloride in the presence of tertiary organic base at temperature and time sufficient to produce the compound of formula I:

(e)(ii) contacting the the S,S-diastereomeric acid addition salt of compound XII with an amount of a tertiary organic base at a temperature and time sufficient to produce a compound of formula XIV:

17. The process of claim 16 wherein the hindered organic amine base is 1,8-diazabicyclo[5,4,0]undec-7-ene or 1,5-diazabicyclo[4.3.0]non-5-ene.

18. The process of claim 16 wherein in step (b), (i) the compound of formula IV is contacted with the compound of formula VII in the presence of piperidine, and 2-butanol at the boiling point of 2-butanol for a time sufficient to substantially completely distill an azetropic mixture of 2-butanol and water to form a reaction product comprising a mixture of the compounds of formulas VIII and IX, and (ii) the reaction mixture is cooled to a temperature in the range of about 20–25° C. and a hindered organic amine base is added and the contacting is continued for for a time sufficient to produce the compound of formula IX substantially free of the E and Z chalcones of formula VIII and essentially free of the cis-isomer of the compound of formula IX.

19. The process of claim 18 wherein the hindered amine base in step (a) is 1,8-diazabicyclo[5.4.0]undec-7-ene.

20. The process of claim 16 wherein in step (e) the tertiary organic base is tri($C_1$–$C_6$) alkylamine, pyridine or N-methylmorpholine.

21. The process of claim 16 wherein in step (e) the tertiary organic amine is triethylamine.

22. The process of claim 16 wherein in step (e)(ii) a suspension the diastereomeric acid addition salt of formula XII in a mixture of an immiscible organic solvent and water at a temperature in the range of about −20° to 25° C. is contacted with tertiary organic base and a stoichiometric excess of aqueous hydrogen chloride for a time sufficient to produce the compound of formula XV:

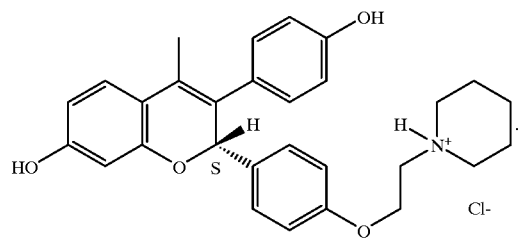

XV

* * * * *